United States Patent [19]

Tom et al.

[11] 4,366,241

[45] Dec. 28, 1982

[54] CONCENTRATING ZONE METHOD IN HETEROGENEOUS IMMUNOASSAYS

[75] Inventors: Henry K. Tom, La Honda; Gerald L. Rowley, Cupertino, both of Calif.

[73] Assignee: Syva Company, Palo Alto, Calif.

[21] Appl. No.: 176,177

[22] Filed: Aug. 7, 1980

[51] Int. Cl.$^3$ .................... G01N 33/54; G01N 33/16; C12Q 1/70

[52] U.S. Cl. ........................................ 435/7; 435/5; 435/805; 435/810; 424/1; 422/56

[58] Field of Search ...................... 435/5, 7, 188, 805, 435/810; 422/55, 56, 61; 23/230 B, 230 R; 424/1, 8, 12

[56] References Cited

U.S. PATENT DOCUMENTS

| | | | |
|---|---|---|---|
| 3,811,840 | 5/1974 | Bauer et al. | 422/56 |
| 4,061,468 | 12/1977 | Lange et al. | 422/56 |
| 4,094,647 | 6/1978 | Deutsch et al. | 435/7 |
| 4,168,146 | 9/1979 | Grubb et al. | 435/7 |
| 4,190,496 | 2/1980 | Rubenstein et al. | 435/7 |
| 4,205,058 | 5/1980 | Wagner | 422/61 |
| 4,226,978 | 10/1980 | Bogwslaski et al. | 435/188 |
| 4,233,402 | 11/1980 | Maggio et al. | 435/7 |

*Primary Examiner*—Thomas G. Wiseman
*Attorney, Agent, or Firm*—Bertram I. Rowland

[57] ABSTRACT

Method and apparatus are provided for performing immunoassays employing a device comprising a relatively small test zone referred to as an immunosorbing zone, and a relatively large liquid absorbing zone in liquid receiving relationship with said immunosorbing zone. The immunosorbing zone includes a member of an immunological pair ("mip")—ligand and antiligand—bound to a support.

A signal producing system is employed in conjunction with said device having as one component a signal label bound to a mip. The signal producing system provides for production of a detectible signal in the immunosorbing zone in relation to the amount of analyte in a sample.

34 Claims, 5 Drawing Figures

U.S. Patent  Dec. 28, 1982  4,366,241
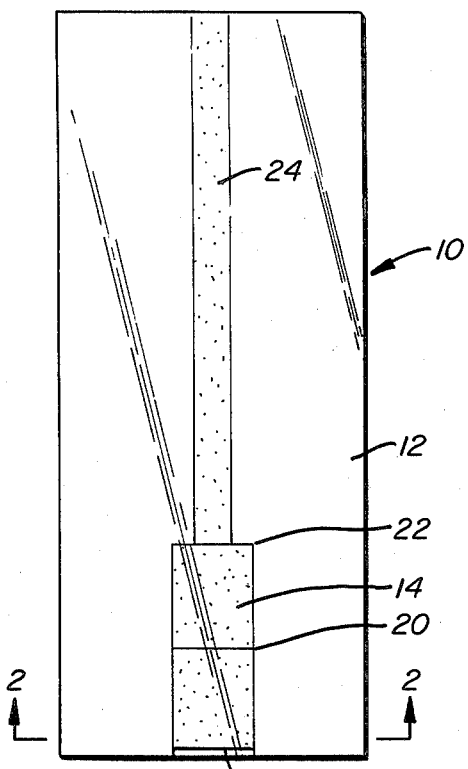
FIG._1.
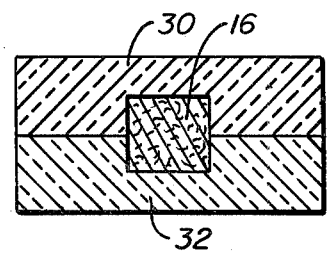
FIG._2.
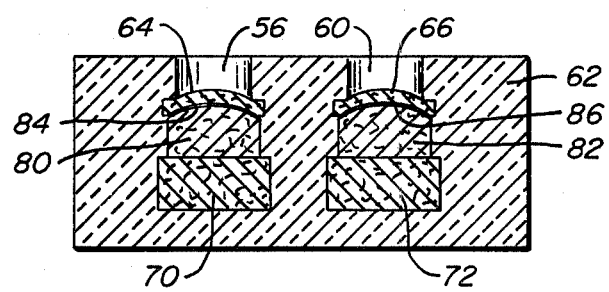
FIG._4.
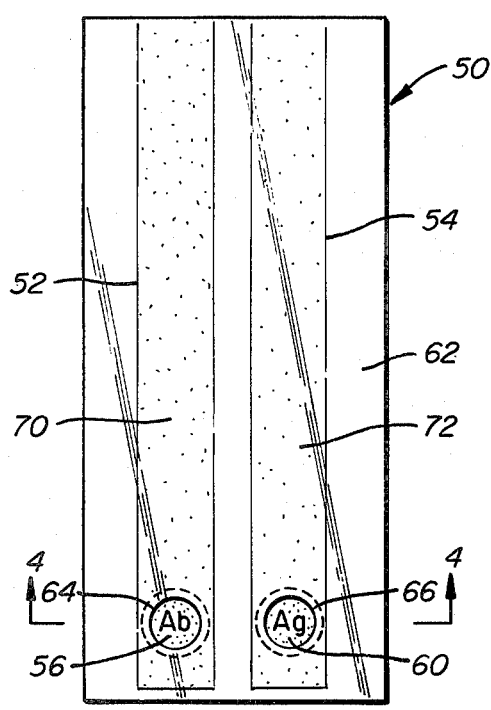
FIG._3.
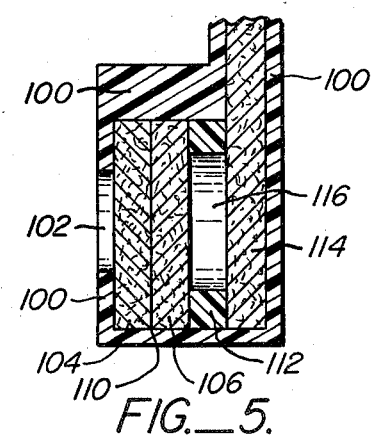
FIG._5.

CONCENTRATING ZONE METHOD IN HETEROGENEOUS IMMUNOASSAYS

BACKGROUND OF THE INVENTION

1. Field of the Invention

The ability to employ naturally occurring receptors or antibodies directed to specific compounds in assaying for the presence of a compound of interest has created a burgeoning immunoassay business. In each of the assays, a homologous pair, usually an immunological pair, involving a ligand and a receptor (antiligand) is involved, wherein one of the members of the immunological pair (mip) is labeled with a label which provides a detectible signal. The immunoassay methodology results in a distribution of the signal label between signal label bound in a complex of the mips and unbound signal label. The differentiation between bound and unbound signal label can be as a result of physical separation of bound from unbound signal label or modulation of the detectible signal between bound and unbound signal label.

For the most part, immunoassays have been directed to quantitative determination of a wide variety of compounds of interest, particularly drugs, in clinical laboratories requiring relatively sophisticated equipment and careful technique. Immunoassays have found less extensive commercial application where semi-quantitative or qualitative results would be acceptable and where the determination would involve non-laboratory personnel, such as in a home or a medical practitioner's office. Even in the clinical laboratory, simple and rapid screening tests employing inexperienced personnel could sever to provide substantial economies.

In developing an immunoassay, there are many considerations. One consideration is to provide substantial differentiation between the observed signal resulting from signal label when bound as compared to unbound. Another consideration is to minimize interference from endogenous materials in the sample suspected of containing the compound of interest. A further consideration is the ease with which the observed signal can be detected and serve to differentiate between concentrations in the concentration range of interest. Other factors include the ease of preparation of the reagents, the accuracy with which samples and reagent solutions must be prepared and measured, the storage stability of the reagents, the number of steps required in the protocol, and the proficiency and accuracy with which each of the steps must be performed. Therefore, in developing an assay which can have application with untrained personnel, such as assays to be performed in the home, in forensic medicine, by medical practitioners, or the like, the observed result should be minimally affected by variations in the manner in which the protocol is carried out or provide for simple techniques for performing the various steps.

2. Description of the Prior Art

U.S. Pat. No. 4,168,146 describes an immunoassay test strip. U.S. Pat. Nos. 3,990,850 and 4,055,394 describe diagnostic test cards. A wide variety of patents and patent applications provide an extensive literature of different techniques for producing detectible signals in immunoassays. The following list is merely illustrative of some of these techniques which can find application in this invention. The following is a list of United States patents and patent applications and a general statement of the type of label involved:

U.S. Pat. Nos. 3,646,346, Radioactive Label; 3,654,090, 3,791,932 and 3,817,838, Enzyme Labels; 3,996,345, Fluorescer-Quencher Labels; 4,062,733, Radioactive Label; 4,067,959, Fluorescer or Enzyme Label; 4,104,029, Chemiluminescent Label; and 4,160,645, Non-Enzymatic Catalyst Label. See U.S. Pat. Nos. 3,966,897 for an electrophoretic technique employing an antibody zone and 4,120,945 for an RIA where labeled analyte is initially bound to a solid support through antibody. U.S. application Ser. No. 893,650, filed Apr. 5, 1978, U.S. Pat. No. 4,233,402, employs enzyme pair labels; 893,910, filed Apr. 5, 1978, U.S. Pat. No. 4,720,450, chemically induced fluorescent label; and 61,099, filed Aug. 26, 1979, U.S. Pat. No. 4,287,300, enzyme anionic charge labels.

SUMMARY OF THE INVENTION

Novel non-chromatographic assay devices and methods employing such devices are described for the determination of members of an immunological pair (mip). The device has an immunosorbing zone to which a mip is fixed against diffusive movement. The immunosorbing zone serves as the entry for the sample and reagent solutions.

In liquid-receiving relationship, either directly or indirectly with the immunosorbing zone and normally extending transversely therefrom is a liquid absorbing zone, which serves to draw liquid through the immunosorbing zone, store liquid and may serve to control the rate at which the liquid is drawn through the immunosorbing zone.

Employed in the method in conjunction with the device is a signal producing system which has a signal label member conjugated to a mip. The immunosorbing zone may include one or more members of the signal producing system which are bound to the zone in a manner to permit or inhibit diffusive movement of the signal producing system component. In accordance with the method protocol, the amount of signal label bound in a detection zone in the immunosorbing zone is related to the amount of analyte in the sample.

The method involves contacting the assay device with the liquid sample to which may have been added one or more components of the signal producing system; followed by contact with one or more successive solutions which contain any remaining components of the signal producing system and serve to wash the immunosorbing zone free of non-specifically bound signal label. The signal producing system provides for a detectible signal in the immunosorbing zone which can be compared to a signal level based on a standard having a known amount of analyte.

BRIEF DESCRIPTION OF THE DRAWINGS

FIG. 1 is a plan view of an assay device;

FIG. 2 is an enlarged cross-sectional view of the assay device of FIG. 1, taken along line 2—2;

FIG. 3 is a plan view of an assay device having a sample test strip and a standard test strip;

FIG. 4 is a cross-sectional view of the assay device of FIG. 3 along lines 4—4.

FIG. 5 is a partial cross-sectional elevation of an alternate embodiment of the subject invention.

DESCRIPTION OF THE SPECIFIC EMBODIMENTS

Method and apparatus are provided for performing immunoassays. The method and apparatus are devised so as to provide for a narrow zone through which relatively large amounts of fluid pass with relatively uniform flow. The zone serves to concentrate both a small amount of analyte in a sample, as well as reagents for producing a detectible signal, while inhibiting the localization of non-specifically bound materials which would result in production of background signal unrelated to the amount of analyte in the medium. Specifically, assay devices are provided which serve to receive a liquid sample and liquid solutions, transmit the solutions through an immunosorbing zone to which a member of an immunological pair (mip) is bound and to draw the liquid and non-specifically bound materials into a storage zone or reservoir. The reagent solutions provide for production of a detectible signal in the immunosorbing zone which may be compared to a standard related to a specific amount of analyte in a sample.

The immunoassay method is adaptable to a wide variety of reagent combinations which have previously been employed in other immunoassays, both homogeneous and heterogeneous. The conditions under which these other assays have been carried out will normally be applicable in the subject method. Thus, the devices of the subject invention allow for a simplicity of protocol as compared to prior art methods, while providing for qualitative or quantitative results analogous to prior art methods. By appropriate choice of the components for producing a detectible signal, the detectible signal may be observed visually or by means of various apparatuses, such as spectrophotometers, fluorometers, scintillation counters, etc.

The analyte to be determined will be a mip. The specificity of the homologous mips provides a means for discriminating between the analyte of interest and other materials which may be in the sample. Thus, by appropriate choice of the mip in the immunosorbing zone, one can provide for specific binding of a component to the immunosorbing zone which results in production of a detectible signal. The amount of such component in the immunosorbing zone can be related to the amount of analyte in the sample.

In addition to the assay device, there will be employed one or more reagents which will comprise the signal producing system. The key reagent in the signal producing system is the one which serves as a signal label and is conjugated to a mip. The choice of protocol will determine whether an increase or decrease in the amount of the conjugate of signal label and mip which is specifically bound in the immunosorbing zone determines the amount of analyte in the assay medium.

DEFINITIONS

Analyte—the compound or composition to be measured, which is a mip and may be a ligand, which is mono- or polyepitopic, that is, having one or plurality of determinant sites, haptenic and antigenic, a single compound or plurality of compounds which share at least one common epitopic or determinant site; or a receptor.

Mip—a member of an immunological pair, consisting of two different molecules, where one of the molecules has an area on the surface or in a cavity which specifically binds to a particular spatial and polar organization of the other molecule. The members of the immunological pair are referred to as ligand and receptor (antiligand) and members of a specific pair are referred to as homologous.

(a) Ligand—any organic compound for which a receptor naturally exists or can be prepared;

(b) Receptor (antiligand)—any macromolecular compound or composition capable of recognizing (having an enhanced binding affinity to) a particular spatial and polar organization of a molecule, i.e. epitopic or determinant site. Illustrative receptors include naturally occurring receptors, e.g. thyroxine binding globulin, antibodies, enzymes, Fab fragments, lectins, and the like. The term antibody is employed in this case as illustrative of and to more generally denote receptor;

(c) Antireceptor—in some situations, a receptor can serve a dual function of binding to a ligand and serving as a ligand to a receptor (antireceptor), such that the ligand and the antireceptor, which cannot bind directly to each other, are joined by the receptor to provide for an immunological linkage. Antireceptors may frequently be antibodies, protein A, rheumatoid factor, Clq. or the like.

Ligand analog—a modified ligand which can compete with the analogous ligand for a receptor, the modification of the ligand providing means to join the ligand analog to another molecule; or where the ligand has a functionality which is used for bonding directly to another molecule, the ligand portion of the conjugate will be referred to as ligand analog. The ligand analog will normally differ from the ligand by more than replacement of a hydrogen with a bond, which links the ligand analog to another molecule, e.g. label or hub. When a plurality of ligand analogs are joined together, particularly by bonding to a central nucleus, e.g. hub, the resulting aggregation will be referred to as a poly(ligand-analog).

Assay device—the assay device has at least one bibulous layer, normally having two or more layers, which will be relatively free of non-specific adsorptivity for the materials of interest. The device has as one element a relatively small immunosorbing zone having a mip non-diffusively fixed in the zone. The mip remains substantially immobilized on a bibulous solid support during the course of the assay; and as a second element a reservoir zone, either directly or indirectly in liquid-receiving relationship with the immunosorbing zone.

(a) Immunosorbing zone—a bibulous solid film, layer or sheet to which a mip is non-diffusively bound; the immunosorbing zone has a relatively small fluid capacity as compared to the total assay device capacity. One or more members of the signal producing system may be bound directly or indirectly to the immunosorbing zone. The immunosorbing zone has specific binding capability for the homologous mip.

Within the immunosorbing zone may be one or more zones in tandem or overlapping. Included within the immunosorbing zone will be a detection zone, which may be the same or different from the zone to which the mip is bound.

(b) Liquid absorbing zone—a bibulous solid material either directly or indirectly in liquid receiving relationship with the immunosorbing zone and acting as a reservoir or storage zone capable of storing a substantially greater liquid volume than the immunosorbing zone. The zone acts as a pump to pull liquid through and out of the immunosorbing zone.

Signal producing system—the signal producing system may have one or more components, at least one component being conjugated to a mip. The signal producing system produces a measurable signal which is detectible by external means, usually the measurement of electromagnetic radiation, which signal will be produced in a detection zone in the immunosorbing zone. For the most part, the signal producing system will involve radioactive substances, enzymes and chromogenic substrates, and chromophores, where chromophores include dyes which absorb light in the ultraviolet or visible region, phosphors, fluorescers, and chemiluminescers. While for the most part the signals can be absorption or emission of electromagnetic radiation, usually in the ultraviolet or visible range, other detectible signals will also find application in particular situations.

Signal generator—the compound which provides for production of the detectible signal. The signal generator may be produced during the assay or be present initially and produce the signal without undergoing any chemical change. Where a chemical reaction is involved, the compound undergoing the reaction to produce the signal is referred to as the signal generator precursor.

Label—the label may be any molecule conjugated to another molecule or support and may be arbitrarily chosen. In the subject invention, the labels will be the mip bound to the assay device as a support and members of the signal producing system whether bound to the mip or to the assay device as a support.

Mip-support conjugate—in the immunosorbing zone, the mip bound to the assay device support, which may be bound covalently or non-covalently, directly or indirectly. The mip is bound substantially permanently to the support, so as not to migrate during the traverse of the sample and reagent solutions through the immunosorbing zone. The mip serves to binds its homologous member to the immunosorbing zone.

Signal label-mip conjugate—a member of the signal producing system, which is directly or indirectly bonded to a mip, which is or becomes bound to the immunosorbing zone to provide for production of a detectible signal in the detection zone.

Signal label-support conjugate—a member of the signal producing system bound, covalently or noncovalently, directly or indirectly, to the immunosorbing zone which acts in conjunction with the signal label-mip conjugate to produce a signal in the detection zone.

METHOD

The subject method employs an assay device in conjunction with a sample solution and usually one or more reagent or wash solutions. The method involves contacting the immunosorbing zone with a sample solution, where the liquid holding capacity of the immunosorbing zone is substantially smaller than the volume of the sample, as well as the portion of the sample which traverses the immunosorbing zone.

The immunosorbing zone has mip fixed to a solid support, where the mip is inhibited from diffusing from the zone. The analyte in the sample solution passing through the immunosorbing zone binds to the mip of the mip-support conjugate and is concentrated in the immunosorbing zone.

The signal label-mip conjugate may be involved in a number of ways: (1) initially present in the immunosorbing zone non-covalently bound through immunological complexation to the mip-support conjugate and displaced by the analyte; (2) present with the sample and competes or acts in concert with the analyte to become bound to the mip-support conjugate; or (3) may be added subsequently.

After contacting the sample, the immunosorbing zone will be contacted with any remaining members of the signal producing system, and as appropriate, wash solutions, where a detectible signal will be developed at the detection zone in relation to the amount of analyte in the medium. In most protocols, the reagent solutions will also serve as wash solutions to minimize the number of steps in the protocol.

The subject method is distinguished from prior art methods which involve diffusion of solutes diffusing to and away from a layer immersed in a liquid. Thus the layer encounters a continuously changing solution composition as solute becomes bound to the layer or dissolves into the liquid. In the subject invention, the mip containing layer in contact with the solution continuously contacts substantially the same solution composition as the solution diffuses through the layer. Thus, the concentrations of solutes in the solution in the mip containing layer remain relatively constant during contact of the immunosorbing zone with a solution.

The structure of the assay device with the immunosorbing zone acting as the entry port can be designed in a variety of ways. The assay device except for the immunosorbing zone must be isolated, normally by a non-permeable barrier, so that the solution is restricted to being absorbed through the immunosorbing zone prior to being absorbed by the liquid absorbing zone. The immunosorbing zone is exposed by an opening in the non-permeable barrier. With this construction, the assay device can be conveniently immersed in a solution.

Alternatively, the solutions may be applied to the immunosorbing zone in a horizontal position, either dropwise, as a slowly flowing stream, or in a container surrounding the immunosorbing zone.

The sample may or may not be subject to prior treatment, but usually will not be treated. When prior treatment is employed, buffer with or without one or more components of the signal producing system or other reagents may be included. When the sample solution is ready for sampling, the immunosorbing zone of the assay device is contacted with the sample and absorbs at least a portion of the sample, so that a substantial proportion of the sample solution enters through and traverses the immunosorbing zone and extends into the storage zone. With the subject device, the volumes of the solutions normally need not be premeasured. The amount of solution absorbed can be controlled by the distance the liquid traverse the liquid absorbing zone.

In this manner, a relatively large sample volume may pass through the immunosorbing zone, resulting in substantial concentration of the analyte in the limited volume of the immunosorbing zone. Limited only by the capacity of the liquid absorbing zone and the binding constants of the homologous mips, lower concentrations of analyte can be detected by permitting larger volumes of sample to be absorbed and transferred through the immunosorbing zone.

The analyte of interest may be present in a wide variety of environments. Analytes of interest include drugs, hormones, macromolecules, and microorganisms, which may be found in physiological fluids, such as blood—whole serum or plasma—urine, cerebral spinal fluid, ocular lens liquid, and saliva; synthetic chemicals;

pollutants in water and air; trace compounds, toxins and microorganisms in food, e.g. milk, meat, poultry and fish; or the like. The fact is that any organic substance which can serve as a ligand or any receptor for which a ligand may be obtained can be determined, so long as such analyte can be introduced into a liquid system in a form in which it can bind to the homologous mip.

Depending upon the protocol, one or more components of the signal producing system may be present with the analyte in the sample solution. A solution having the signal label-mip conjugate may be followed by at least one additional solution, to ensure the removal of non-specific binding of the signal label-mip conjugate in the immunosorbing zone and/or introduce remaining components of the signal producing system. Where more than one component is included in the signal producing system, conveniently the signal label-mip conjugate solution can be sorbed in the immunosorbing zone prior to the addition of the remaining members of the signal producing system in a subsequent reagent solution. The subsequent reagent solution then serves as a wash to remove non-specifically bound signal label-mip conjugate. Alternatively, nothing is added to the sample which is contacted first, and then followed by one or more additional solutions containing the signal label-mip conjugate and the other components of the signal producing system.

A wide variety of protocols will be available, the particular configuration being subject to: the nature of the analyte, i.e., whether it is a mono- or polyepitopic ligand or a receptor; the nature of the signal label-mip conjugate; and the nature and number of components in the signal producing system. Therefore, a number of illustrative examples of protocols will be given, which are not exhaustive, but are rather embodiments of protocols which serve to indicate the numerous opportunities for variation.

The following Table I indicates the various combinations of analytes and reagents which may be employed in the subject invention to provide a signal in the immunosorbing zone related to the amount of analyte.

TABLE I

| | Mips In Signal Producing System | | | |
|---|---|---|---|---|
| Analyte | Mip Support Conjugate | Signal Label Mip | Other Mip | Preferred Protocols |
| 1. H | $Ab_H$ | L-H | | 1,2 |
| 2. H | $Ab_H$ | L-H | $Ab_H$ | 2 |
| 3. H | H | $L-Ab_H$ | | 2 |
| 4. Ag | $Ab_{Ag}$ | L-Ag | | 1,2 |
| 5. Ag | $Ab_{Ag}$ | L-Ab | | 1 |
| 6. Ag | Ag | $L-Ab_{Ag}$ | | 2 |
| 7. $Ab_H$ | H | $L-Ab_H$ | | 1,2 |
| 8. $Ab_H$ | H | $L-Ab_H$ | H | 2 |
| 9. $Ab_H$ | H | $L-Ab_{Ab}$ | | 1 |
| 10. $Ab_H$ | H | L-H | | 1 |
| 11. $Ab_H$ | $Ab_H$ | L-H | | 2 |
| 12. $Ab_{Ag}$ | Ag | $L-Ab_{Ag}$ | | 1,2 |
| 13. $Ab_{Ag}$ | Ag | L-Ag | | 1 |
| 14. $Ab_{Ag}$ | Ag | $L-Ab_{Ab}$ | | 1 |
| 15. $Ab_{Ag}$ | $Ab_{Ag}$ | L-Ag | | 2 |
| 16. Ag | $Ab_{Ag}$ | $L-Ab_{Ab}$ | $Ab_{Ag}$ | 1 |
| 17. H | $Ab_H$ | $L-Ab_{Ab}$ | $Ab_H$ | 1 |

Protocol 1: Contact sample and assay device prior to contact with other parts of signal producing system.
Protocol 2: Combine sample with mip components of signal producing system prior to or simultaneously with contact with assay device.
H—monoepitopic ligand
Ag—polyepitopic ligand
Ab—receptor, normally an antibody; subscript indicates homologous mip
L—label The various combinations can involve two basic protocols. Protocol 2 involves combining the sample and mip components of the signal producing system and contacting the assay device with the resulting solution. For some applications, the assay device strip would then be contacted with a wash solution that optionally would contain the other components of the signal producing system to ensure the complete removal of non-specific binding mip. Alternatively, in protocol 1 the assay device could be contacted with the sample, followed by contact with the mip component of the signal producing system, followed optionally by a wash solution which if employed would usually contain the other components of the signal producing system. Additionally, with 1 and 7 the L-mip could be initially bound to the mip-support conjugate, so that upon immersion in the sample the L-mip would be displaced by the hapten analyte. No further steps would be necessary where the signal label is a radioactive label or fluorescer.

For combinations 2 and 8 one would combine the sample with the combined signal label-mip and other mip and contact the assay device with the resulting solution.

Depending on the nature of the signal label and signal producing system, one would observe the signal, by irradiating with light for a fluorescer and observing the level of fluorescence; providing for a catalyst system to produce a dye, fluorescer, or chemiluminescence, where the dye could be observed visually or in a spectrophotometer and the fluorescer could be observed visually or in a fluorometer; or in the case of chemiluminescence or a radioactive label, by employing a radiation counter. Where the appropriate equipment is not available, it will normally be desirable to have a chromophore produced which results in a visible color. Where sophisticated equipment is involved, any of the techniques is applicable.

After each combination of reagents, an incubation step may be involved. Incubation steps involving combining solutions can vary from about 5 sec to 16 hrs or more, generally varying from about 1 min to 1 hr, more usually from about 5 min to 30 min. By contrast, the time during which the assay device is contacted with each solution will depend upon the volume of the solution to be sorbed and the rate at which it diffuses into the liquid absorbing zone. This time will be controlled in accordance with the concentration of the mip in the solution, the concentration of mip in the area of the immunosorbing zone, the binding constant of the homologous mips, the rate of production of signal, and the like. The manner in which the time for diffusion of the solutions through the immunosorbing zone may be controlled will involve the composition, construction, size and shape of the immunosorbing and liquid absorbing zones, the temperature, the solvent, and the like. In view of the wide variety of opportunities for use of the subject method and devices, no particular time range ascribed to the subject metod would be meaningful.

For the most part, the various solution combinings, contacting of solutions with the assay device, and readings will be carried out at a temperature in the range of about 0° to 50° C., more usually in the range of about 15° to 40° C. For the combining of the various reagents, as well as the incubation steps, temperatures will generally range from about 15° to 50° C., frequently 20° to 35° C., and conveniently ambient temperatures. Depending upon whether the measurement is qualitative, semiquantitative or quantitative, the temperature may be controlled or uncontrolled, conveniently employing ambient temperatures. Frequently, when employing ambient temperatures, one or more control strips may be employed for comparison with the observed signal from the sample strip.

The solutions which are employed will normally be buffered at a pH in the range of about 5 to 11, more usually 5 to 10, and preferably about 6 to 9. The pH is chosen so as to maintain a significant level of specific binding by the mips while optimizing signal producing efficiency. Obviously, various pH's may be used with different solutions. Various buffers may be used to achieve the desired pH and maintain the desired pH during the determination. Illustrative buffers include borate, phosphate, carbonate, tris, barbital, and the like. The particular buffer employed is not critical to this invention, but in individual assays, one buffer may be preferred over another.

The concentration of analyte which may be assayed will generally vary from about $10^{-4}$ to $10^{-15}$, more usually from about $10^{-6}$ to $10^{-13}$ M. Considerations such as whether the assay is qualitative, semi-quantitative, or quantitative, the particular detection technique and the concentration of the analyte of interest will normally determine the concentration of the other reagents.

The concentrations of various reagents will vary widely depending upon which protocols are employed, the nature of the analyte, the mip in the immunosorbing zone, the required sensitivity of the assay, and the like. In some instances, large excesses of one or the other of the mips may be employed, while in some protocols the sensitivity of the assay will be responsive to variations in the mip ratios.

By way of illustration, if the analyte is a polyepitopic antigen, one could have excesses of antiligand as antiligand-support conjugate and as signal label-antiligand conjugate, without seriously affecting the sensitivity of the assay, provided that the assay device is first contacted with the sample, followed by contact with the signal producing system solution, desirably followed by a wash solution. Where antiligand is the analyte and the protocol involves the combination of the analyte and catalyst-antiligand conjugate, prior to contacting the antigen-support conjugate, the sensitivity of the assay will be related to the ratio of the analyte and catalyst-antiligand concentration.

In addition to the considerations involving the protocol, the concentration of the reagents will depend on the binding constant of the antiligand, or the binding constant profile where an antiserum is used, as well as the required sensitivity of the assay. Desirably, when feasible, the concentration of the signal label-mip will be sufficiently low to minimize non-specific binding or occlusion within the immunosorbing zone, particularly the detection zone.

In view of the wide differences in ratios resulting from variations in the properties and nature of the various reagents, the molar ratios can only be very broadly stated. For example, based on the analyte range of interest, the number of molecules of signal label-mip conjugate drawn into the immunosorbing zone will usually be not less than about 0.1 times the minimum number of moles of analyte based on binding sites and not more than about 1,000 times the maximum moles of analyte based on binding sites drawn into the immunosorbing zone, more usually from about 0.1 to 100 times the moles of analyte based on binding sites. So far as the mip of the mip-support conjugate, there will usually be not less than about 0.001 times the minimum number of moles of analyte based on binding sites drawn into the immunosorbing zone. As already indicated, depending upon the protocols, there can be large excesses over stoichiometric. The amount of mip in the immunosorbing zone will be at least sufficient to provide a detectible signal when fully bound by signal label mip conjugate. (The above reference to sample or analyte intends the volume or number which traverses the immunosorbing zone, and not the total volume of the sample solution or total amount of analyte which contacts the assay device.)

In developing protocols for the method, certain basic considerations will govern the order of addition and the combinations of reagents. Where a large excess of signal label-mip conjugate is employed, one will usually not combine the signal label-mip conjugate with the analyte prior to combining the analyte with the assay device. Where the signal label is a catalyst, one will normally not combine the signal label-mip with the signal label substrates under conditions in which a reaction will take place prior to the binding of the signal label-mip to the test device. Chemiluminescence involves similar considerations as those for catalyst labels.

Various protocols will have different degrees of complexity. Considerations affecting complexity are volumetric measurements, number of steps, timing accuracy, and probability of background interference. Usually, premeasurement will be avoided and while the device may be contacted with only one solution, usually it will be contacted with at least two solutions. Normally, after contacting the device with the signal label-mip conjugate, a subsequent contact with a wash solution containing reagents, such as enzyme substrates will often be employed. In this way, one can ensure the substantial absence of nonspecific binding and occlusion of the signal label-mip in the immunosorbing zone. The subject method therefore offers particular advantages, where a catalyst, particularly an enzyme, is involved. In prior methods, a separate wash step was required. In the subject invention, the addition of reagents serves as a wash.

The choice in providing for a ligand or receptor in the immunosorbing zone will depend upon a number of factors. When a polyepitopic ligand is the analyte, the use of catalyst-mip conjugate where the mip is antibody to the receptor (Protocols 16 and 17) enhances the assay response by permitting many catalysts to become bound to each molecule of the analyte in the immunosorbing zone. However, usually the assay device must then be contacted with at least three separate solutions in the order of sample, followed by antibody, followed by signal label-mip. The purity of the ligand or receptor will also be of significance. While contaminants in antigen or antibody used for preparing the mip-support conjugate will rarely affect the assay, functionalization of very impure antigens or antibodies with the signal label may be undesirable. However, the subject invention provides for a mechanism for removing the signal label bound to other than a mip from the immunosorbing zone.

As previously indicated, a further consideration is the simplicity of the protocol. In the subject invention, it is desirable to minimize the number of measurements which could have a significant effect on the assay result. Where the assay device is first contacted with the sample alone it is possible to avoid any measurement.

Where the sample is combined with other solutions, it is desirable to limit the required measurements to the size of the sample and, as appropriate, its subsequent dilution to provide the assay sample. Particularly, for semi-quntitative or qualitative results, the addition of the remaining reagents should allow for substantial variation in volumes and concentrations without affecting the assay result.

An illustration of the situation is the use of an assay device having antibody in the immunosorbing zone. The signal label-mip also employs antibody and the sample is an antigen. By employing two steps, first contacting the assay device with the sample, followed by contacting the assay device with the signal label-mip conjugate, the amount of signal label-mip conjugate greater than a predetermined minimum will not significantly affect the assay result, when a subsequent step is employed to reduce occluded and non-specifically bound signal label-mip. By contrast, if one had combined the sample and signal label-antibody conjugate initially, where there is a large excess of signal label-antibody, this would result in inhibiting the binding of antigen to the antibody-support conjugate in the immunosorbing zone.

To further illustrate the subject invention, exemplary protocols will be described using mono-, polyepitopic or receptor analytes and as signal labels: a signal label not requiring the addition of other chemical reagents for production of a signal; a signal label requiring additional reagents for production of a signal; and a signal label which requires additional reagents for production of a signal and interacts with a component of the signal producing system initially present in the immunosorbing zone of the assay device. Also described will be a protocol requiring a complex immunosorbing zone, where the signal label-mip conjugate is initially present in the immunosorbing zone.

The first exemplary protocol will employ a hapten (monoepitopic ligand) as the analyte and a fluorescer as the signal label, where the fluorescer is bound to a hapten analog. In this protocol, the specimen suspected of containing the hapten is combined with a buffered solution of the hapten-fluorescer reagent to a predetermined volume. The assay device containing antihapten in the immunosorbing zone is immersed in the sample and the assay sample solution sorbed to a predetermined distance in the liquid absorbing zone. The assay device is then removed from the assay sample solution and introduced into a buffer solution, where the buffer solution courses through the immunosorbing zone to ensure the complete removal of any non-specifically bound hapten-fluorescer reagent in the immunosorbing zone. If the concentration of hapten-fluorescer in the reagent solution is sufficiently low compared to the amount of hapten-fluorescer bound for a positive result, then the washing step may be dispensed with. The assay device may then be introduced into a fluorometer and the fluorescence determined.

Desirably, a standard assay device could be employed which would be carried through the same steps as the assay device for the specimen. The standard assay device would have a predetermined amount of antibody in the immunosorbing zone and when introduced into the reagent solution in the absence of hapten analyte would absorb an amount of hapten-fluorescer reagent which would relate to a specific concentration of hapten. Thus, by comparing the standard with the specimen, one could determine whether the amount of hapten was above or below the predetermined level. Alternatively a standard assay device could be employed that could be contacted with the analyte but would give a standard response unrelated to the amount of analyte.

It should be noted that the washings with the assay device of the subject invention differ from the washings employed in other assays employing dipsticks or test strips. In other washings, the test strip is introduced into a solution which is free of any reagent and any non-specifically bound materials allowed to diffuse from the test strip into the solution. It must thereafter be removed from the wash solution. By contrast, in the subject invention, the solution passing through the immunosorbing zone carries non-specifically bound materials with it into the liquid absorbing zone, so that the immunosorbing zone is continuously contacted with fresh solution free of non-specifically binding signal label. Thus, with small volumes, one can provide for efficient removal of non-specifically bound signal label from the immunosorbing zone without contaminating the solution.

In the second protocol, an antigen is employed, where the antigen may act as a bridge between antiligand in the immunosorbing zone and signal label (in this case an enzyme) bound to antibody. In this protocol, the assay device having antiligand is immersed in a specimen sample suspected of having ligand, usually undiluted. A predetermined amount of the assay sample solution diffuses through the immunosorbing zone into the liquid absorbing zone, where antigen in the assay sample solution becomes bound to the antiligand in the immunosorbing zone in proportion to the concentration of antigen in the solution. The assay device is removed and immersed in a buffered reagent solution, which can have a large excess of enzyme-antiligand as the reagent.

As the reagent solution diffuses through the immunosorbing zone, the enzyme-antiligand will bind to any ligand bound in the immunosorbing zone. The volume of liquid sorbed may be determined by the distance the solvent front travels. Relatively short incubation times are necessary for the binding of the enzyme-antiligand reagent to the antigen in the immunosorbing zone, since the subject method provides for continuously replenishing the reagent to the immunosorbing zone at a relatively high reagent concentration. After the predetermined volume has been sorbed by the assay device, the assay device is removed and introduced into a substrate solution. Enzyme catalysis results in transformation of the substrate to a colored product, which may be deposited in the immunosorbing zone. Once again, one can control the volume of the substrate solution which traverses the immunosorbing zone by following the solvent front in the liquid absorbing zone.

One could have a standard assay device by having an assay device having a predetermined amount of antigen in place of antibody present in the immunosorbing zone. The standard assay device would be treated in the identical manner.

In the third protocol, antibody is the analyte and the signal producing system will involve two enzymes. The signal label-mip reagent will be an enzyme whose substrate is the product of an enzyme bound in the immunosorbing zone. The assay device will have antibody as the mip in the immunosorbing zone. The sample would be mixed with a predetermined volume of the enzyme-antigen regent and incubated for sufficient time to ensure the substantially complete binding of any antibody in the sample with the enzyme-antigen reagent. The assay device would then be introduced into the assay sample solution and the solution sorbed through the immunosorbing zone, so that any remaining unbound enzyme-antigen would become bound in the immunosorbing zone.

After a predetermined volume has moved through the immunosorbing zone as evidenced by movement of the solvent front in the liquid absorbing zone, the assay device would be removed and placed in a substrate solution. The substrate solution would have substrate for the enzyme that is bound to the assay device, as well as any additional reagents necessary for the two enzymes, except for the substrate of the enzyme-antigen reagent, which is the product of the enzyme bound to the device. A wash would normally not be necessary in this mode, since the substrate solution would wash the immunosorbing zone free of any of the enzyme-antigen-antibody complex. A predetermined volume of the substrate solution will move through the immunosorbing zone providing a colored product in the immunosorbing zone. Alternatively, where washing is not required, the substrate solution could be combined with the sample and enzyme-antigen solution followed by immersing the assay device in the mixture.

Finally, one could employ a complex immunosorbing zone having a plurality of overlapping or tandem layers. Where the analyte is a hapten, the first layer which is initially contacted by the solutions would have antihapten complexed with an enzyme-hapten conjugate. An intermediate layer may be provided to inhibit transfer of compounds from the third to the first layer. The third layer would have a reagent to cause the signal producing substances to be formed on that layer as for example enzyme, anti(signal label), antienzyme, etc.

In this case, to prevent signal production in the first layer, a second enzyme is provided which is bound to the third layer. The second enzyme is characterized by producing a product which is the substrate for the enzyme of the enzyme-hapten conjugate. The intermediate layer inhibits the second enzyme product from migrating to the first layer.

For illustrative purposes, the second enzyme will be illustrated by glucose oxidase and the enzyme of the enzyme-hapten conjugate by horse radish peroxidase (HRP). The HRP-hapten is bound to antihapten in the first layer of the immunosorbing zone, while glucose oxidase, and anti-HRP, are covalently bonded to the third layer. Catalase is present in the intermediate layer or only two layers need be involved and catalase could be present in the first layer. The catalase serves to destroy any adventitious hydrogen peroxide which might migrate from the third layer to the first layer.

The assay is performed by adding the sample solution to the first layer which overlays the other layers, so that the solution migrates downwardly. Hapten in the sample displaces HRP-hapten in the first layer, so that the HRP-hapten migrates downwardly to the third layer and is captured by anti-HRP. The sample solution is combined with or followed by a reagent solution containing glucose and a dye precursor. The glucose and dye precursor will migrate to the third layer carrying any non-specifically bound HRP-hapten in the first two layers to the third layer. In the third layer, glucose will serve to form hydrogen peroxide, which in turn will react with the dye precursor in a reaction catalysed by HRP to produce a dye. The intensity of the color produced in the third layer (detection zone) will be related to the amount of hapten in the sample. The assay device would be viewed from the rear where the third layer would be observable.

The standards employed may be widely varied with the assay devices of the subject invention. In some instances, it will be sufficient to provide a series of graduated colors which can be compared with the color produced on the assay device. For a more quantitative result, it would be desirable to have one or more assay devices having a predetermined amount of a mip present which assay devices would then be treated in substantially the same manner as the assay device employed with the specimen. Where the mip on the assay device is the same as the analyte, one could employ the assay device in the idential manner. Where the mip on the assay device is the homologous mip to the analyte, one would normally avoid combining the standard assay device with the specimen.

By having a plurality of lanes on the assay device with a plurality of mips from different immunological pairs, one could run a simultaneous test for a number of different analytes. Except that the immunosorbing zone would be divided into a plurality of areas containing different ligands or different antiligands, the method and reagents would be the same.

MATERIALS

The components employed in this subject assay will be the assay device, the analyte, the signal producing system, which includes the signal label-mip conjugate, and as appropriate one of the other mips.

Assay Device

The assay device has two parts: an immunosorbing zone which uniquely serves as the inlet port for the solutions, and a liquid absorbing zone which serves to draw the solutions through the immunosorbing zone and store the solutions as appropriate. The assay device may have many configurations. One configuration is a test strip involving an extended bibulous strip as the liquid absorbing zone and a narrow region in the same plane or preferably as a contiguous layer which serves as the immunosorbing zone.

The test strip is an elongated device, having two primary portions, a relatively small immunosorbing zone, and a relatively large liquid absorbing zone. The immunosorbing zone will normally be kept as small as possible commensurate with its function. The immunosorbing zone has as its primary distinction mip within its boundaries and optionally one or more members of the signal producing system.

While the dimensions of the test strip may vary widely, the length will normally be substantially greater than the width at least two times greater than the width, and may be ten times or more greater than the width, and the width and thickness may be regular or irregular. The strip may be a single material or a plurality of materials, so long as each of the zones is in liquid receiving relationship with the adjacent zone. The materials may draw liquid by absorption, normally without any substantial adsorption or chromatographic effect. That is, all of the materials, except for the mips involved, will flow relatively evenly and freely through the zones.

Various natural or synthetic materials may be employed, which may be individual materials or combinations of materials, which may be organic, inorganic, or combinations thereof. Where more than one layer is involved different layers may have different properties for different functions. Immunosorbent layers need not have high capacity for retaining liquid, as contracted with liquid absorbents. For detection of electromagnetic radiation, the detection zone may be opaque, or transluscent or preferably transparent.

Included among materials which may find use are polysaccharides, e.g. cellulose materials, such as paper and cellulose acetate; silica, inorganic materials, such as deactivated alumina, diatomaceous earth, $MgSO_4$, or other inorganic finely divided material conveniently substantially uniformly dispersed in a porous polymer matrix, with polymers such as vinyl chloride, vinyl chloride-propylene copolymer, and vinyl chloride-vinyl acetate copolymer; cloth, both naturally occurring e.g. cotton and synthetic e.g. nylon cloth; porous gels, e.g. silica gel, agarose, dextran, and gelatin; polymeric films, e.g. polyacrylamide; or the like. The important features of the assay device material are that they are able to absorb liquid, particularly aqueous solutions, without substantially impeding the movement of the solutes employed in the assay. In effect, the materials are bibulous; they are porous and allow the flow of solutions; the materials for the immunosorbent layers are preferably non-chromatographic; they have reasonable strength or strength can be imparted by means of a support, and they do not interfere with production of the signal by the signal generator.

The liquid absorbing zone is protected from direct contact with the sample and reagent solutions. This will be conveniently achieved by having the immunosorbing zone as the only exposed portion of the test strip or having the area around the immunosorbing zone enclosed to prevent sample or other reagent solution contact with the liquid absorbing zone.

One function of the immunosorbing zone is to contact the various solutions and draw the solutions into the test strip. The immunosorbing zone may be the edge of the test strip, or may be an exposed zone on the face of the test strip, or may extend beyond, be aligned with or internal to an impermeable protective cover. A significant factor in the construction is that the flow of solution through the exposed surface is reasonably uniform.

The exposed surface of the immunosorbing zone will generally be not less than at least about 1 mm in its smallest dimension and will usually be at least about 1.5, more usually at least about 2 mm in its smallest dimension. The immunosorbing zone will usually be not greater than about 2 cm in its largest dimension, generally being about 0.2 to 1 cm in its largest dimension. The thickness of the immunosorbing zone will generally vary from about $10\mu$–5 mm, most usually $50\mu$ to about 3 mm, preferably about 0.2 mm to 1 mm.

The immunosorbing zone may be any configuration, e.g. circular, elliptical, square, rectangular, or irregular. The significant factor is that the surface of the detection zone can be scanned for signal. The surface will normally be planar or slightly curved, either concave or convex, with no more than about 60° of arc.

The immunosorbing zone may be a single layer or a plurality of layers and may produce the signal in the upper or lower portion of the immunosorbing zone (upper and lower relate to upstream and downstream in relation to the flow of liquid). The immunosorbing zone includes as a single layer or the upper layer, mip bound to a bibulous support. In some protocols the signal label-mip conjugate may be complexed with the mip-support conjugate.

Where there are multiple layers, and the detection zone is a separate layer a lower layer will have anti(signal label) or a member of the signal producing system non-diffusively bound to a bibulous support. The lower layer conjugate serves to capture the signal label-mip conjugate or products produced by the signal label-mip conjugate which migrate from the mip-support conjugate layer. Signal labels and anti(signal labels) are chosen so that the anti(signal label) will not significantly interfere with production of signal in the lower layer. Reactants are also chosen to generate a readily detectable signal.

One or more additional layers may be involved, particularly between the mip-support conjugate layer and the lower layer. These layers may serve as barriers to inhibit migration of components of the signal producing system from the lower to the upper layer; as filters; for flow control; or the like.

The flow through the immunosorbing zone should be reasonable uniform. Many bibulous materials will be non-uniform, so that flow through the mip containing entry zone may vary from region to region. To offset the inhomogeneity of layers in the immunosorbing zone, various composite structures may be employed.

One structure employs a first bibulous layer to which mip is bound and which resists the through flow of liquid resulting in a substantial pressure differential across the layer. Behind the layer is a relatively open layer providing minimal resistance to flow. This second layer is intermediate the first layer and the liquid absorbing zone.

Another construction is to have three layers, where the first mip containing layer has relatively low resistance to liquid flow, but is backed by a second layer in uniform contact with the first layer, which second layer is substantially more resistive to liquid flow. This results in impeding the rapid flow through one or more regions of the mip contining layer, resulting in a more uniform flow through the first layer. The second layer is followed by a porous layer which does not resist flow.

Each of the layers will be uniformly pressed together to avoid the occurrence of flow paths. A wide variety of compositions of known flow characteristics can be used for constructing the composite structure.

Alternatively for low resistance to flow a spacer may be used which defines an area behind the immunosorbent layer that permits flow normal to and lateral to the immunosorbent layer surface.

Materials which may be used for low flow resistance include paper; nylon, wire, glass or polyolefin mesh or mat; or cotton or the like. The shape should be varied to ensure good uniform contact with the bounding layers, being flat, concave or convex, where the two opposing surfaces may be the same or different.

The upper and/or lower layer may serve as the detection zone for determining the detectable signal. If desired, detectable signal could be produced in both layers, so that two values associated with the amount of analyte could be measured to provide an internal check.

The liquid absorbing zone is in liquid receiving contact with the immunosorbing zone. The liquid absorbing zone provides a plurality of functions. The first function is to serve as a receptacle or storage area for the fluid imbibed by the immunosorbing zone. A second function which can be served but need not, is to control the rate at which the fluid traverses the immunosorbing zone. Where the liquid absorbing zone has a small dimension or is of a different material from the immunosorbing zone, it can act to control the rate at which fluid passes through the immunosorbing zone.

By having irregular dimensions, it can further act to provide for different rates depending upon whether the sample or reagent solutions are being imbibed.

A further function for the liquid absorbing zone is to measure the amount of liquid which is imbibed. By providing for graduations at sequential positions extending away from the immunosorbing zone and along the liquid absorbing zone, one can determine when the solvent front is at a certain position and remove the test strip from the solution. Alternatively, one can provide for dyes which will become colored upon dissolution in or contact with the solvent front to provide a clear signal that the test strip should be removed. For example, pH indicators could be used. Any technique which provides a clear indication of the presence of the solvent front can be employed.

In a test strip, the liquid absorbing zone will generally have a length of at least about 1.5 usually 2 cm and not more than about 30 cm, usually not more than about 20 cm. The width may vary from about 0.1 mm to about 3 cm. These dimensions are primarily for control of the rate and amount of solution imbibed and for convenience in handling and providing for ease of observation of the solvent front. The thickness will generally be about 0.1 mm to 5 mm, usually from about 0.5 to 3 mm.

The liquid absorbing zone may be partially or substantially completely enclosed in a protective casing, conveniently a clear or partially or in some situations completely opaque casing. While the entire liquid absorbing zone need not be encased, a sufficient portion of it should be covered to prevent the liquid absorbing zone from directly contacting the sample solution. In almost all cases it will be necessary that a uniform amount of the sample solution pass through the immunosorbing zone. This can be best achieved by avoiding contact of the liquid absorbing zone with the assay sample solution.

Depending upon the particular protocols involved and the construction of the test strip, the enclosure may be removable or irremovable, may provide for one or more windows and will normally be of a sturdy inert impermeable material which will provide mechanical protection for the bibulous material comprising the various zones and will not interfere with the performance of the assay. Normally an air opening will be provided to prevent the entrapment of air within the enclosure.

In FIGS. 1 and 2, a test strip device 10 is shown with plastic enclosure 12, enclosing a bibulous shovel shaped strip 14. The butt end 16 of the strip is slightly internal of the plastic enclosure 12, so as to be protected from mechanical contact and deterioration. The butt end 16 serves as an immunosorbing zone, with mip bonded to the butt end 16 to a sufficient depth, so that the development of the signal by the signal label can be readily detected. The strip 14 is graduated at 20 and 22 to allow for accurate measurement of the volume of the sample solution and reagent solutions which have traversed the immunosorbing zone 16. The strip 14 has a narrow extended strip 24 which controls the rate of flow of the last solution. The strip 24 extends to an opening 26 in the plastic enclosure 12 which allows for the escape of air as the solutions move up the strip 14. The enclosure 12 is comprised of a front sheet 30 and a back sheet 32, with a clear front sheet 30 to allow for observing the movement of the fluids up the bibulous strip 14.

In performing the assay, the strip need only be dipped into a sample solution and removed when the sample front has reached graduation 20. The test strip 10 is then removed from the sample solution and introduced into a reagent solution and maintained in the reagent solution, until the solvent front has reached graduation 22. The test strip is then removed from the reagent solution and introduced into a wash solution until a sufficient amount of the wash solution has passed through the immunosorbing zone as evidenced by the solvent front moving along the narrow extended strip 24.

The immunosorbing zone butt end 16 may then be observed for production of a detectible signal as evidence of any analyte being present in the sample.

In FIGS. 3 and 4, a test strip device 50 is depicted having two strips, a specimen testing member 52 and a standard strip member 54. Ports 56 and 60 provide openings in the plastic enclosure 62. Immunoabsorbing disk 64 would have antibody bound to it (indicated by the letters Ab) and the immunosorbing disk 66 of the standard 54 would have antigen bound to it (indicated by the letters Ag) in a predetermined amount to provide for a signal level related to an antigen concentration. The bibulous strips 70 and 72, for example, cellulose or paper strips, extend from the immunosorbing zones 64 and 66, respectively, beyond the enclosure 62 to openings 74 and 76 in the plastic enclosure 62 which allow for escape of air from the enclosure. The bottom ends of 70 and 72 are protected from solution.

The immunosorbing disks 64 and 66 are seated on porous spacers 80 and 82 respectively. The porous spacers are inert and substantially non-resistant to fluid flow. There is substantially uniform contact between the immunosorbent zone disks 64 and 66 and the surfaces 84 and 86 of the porous spacers 80 and 82. Thus, solutions exiting from the immunosorbing zone disks 64 and 66 encounter substantially no resistance to their flow.

The spacers 80 and 82 are bounded downstream by the liquid absorbing strips 70 and 72 which absorb the liquid from the spacers 80 and 82 respectively, acting as pumps to withdraw the liquid as the spacers fill with liquid. The above constructions for the specimen and standard are encased in a plastic holder which can be made of one or two or more parts and assembled to hold the various parts of the test strip in alignment and liquid receiving relationship.

In FIG. 5 is depicted an alternative embodiment of the subject test strip device. In this embodiment, the immunosorbing zone and a portion of the liquid absorbing zone are shown. An enclosure 100 is provided with window 102. An immunosorbing bibulous disk 104 having mip bound to it serves as the entry port for sample and solutions. The bibulous disk should be relatively uniform in its liquid absorbing properties, but relatively non-resistant to the flow of liquid through the disk. Immediately behind the immunosorbing disk 104 is a bibulous liquid flow resistant disk 106, which has greater resistance to liquid flow than the immunosorbing disk 104. The two disks, 104 and 106, are uniformly pressed against each other at the interface 110.

Behind the flow resistant disk 106 is spacer 112, which is a ring to allow the free flow of liquid between the flow resistant disk 106 and the liquid absorbing strip 114.

When the device is introduced into a sample or reagent solution, the immunosorbing disk 104 will rapidly absorb the liquid which will move through the disk and encounter the more resistant disk 106. The disk 106 will control the rate of flow. Thus, inhomogeneities present in the immunosorbing disk 104 will not result in rapid flow through one or more hot spots, inhibiting lack of uniformity of liquid flow through the immunosorbing disk 104. After the solution has passed through the flow resistant disk 106, it will continue through the open space 116 of ring 112 and be absorbed by the liquid absorbing strip 114.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:

protamines
    histones
    albumins
    globulins
    scleroproteins
    phosphoproteins
    mucoproteins
    chromoproteins
    lipoproteins
    nucleoproteins
    glycoproteins
    proteoglycans
    unclassified proteins, e.g. somatotropin, prolactin, insulin, pepsin A number of proteins found in the human plasma are important clinically and include:

Prealbumin
    Albumin
    $\alpha_1$-Lipoprotein
    $\alpha_1$-Acid glycoprotein
    $\alpha_1$-Antitrypsin
    $\alpha_1$-Glycoprotein
    Transcortin
    4.6S-Postalbumin
    Tryptophan-poor
        $\alpha_1$-glycoprotein
    $\alpha_1\chi$-Glycoprotein
    Thyroxin-binding globulin
    Inter-$\alpha$-trypsin-inhibitor
    Gc-globulin
        (Gc 1-1)
        (Gc 2-1)
        (Gc 2-2)
    Haptoglobin
        (Hp 1-1)
        (Hp 2-1)
        (Hp 2-2)
    Ceruloplasmin
    Cholinesterase
    $\alpha_2$-Lipoprotein(s)
    Myoglobin
    C-Reactive Protein
    $\alpha_2$-Macroglobulin
    $\alpha_2$-HS-glycoprotein
    Zn-$\alpha_2$-glycoprotein
    $\alpha_2$-Neuramino-glycoprotein
    Erythropoietin
    $\beta$-lipoprotein
    Transferrin
    Hemopexin
    Fibrinogen
    Plasminogen
    $\beta_2$-glycoprotein I
    $\beta_2$-glycoprotein II
    Immunoglobulin G
        (IgG) or $\gamma$G-globulin
    Mol. formula:
        $\gamma_2\kappa_2$ or $\gamma_2\lambda_2$
    Immunoglobulin A (IgA)
        or $\gamma$A-globulin
    Mol. formula:
        $(\alpha_2\kappa_2)^n$ or $(\alpha_2\lambda_2)^n$
    Immunoglobulin M
        (IgM) or $\gamma$M-globulin
    Mol. formula:
        $(\mu_2\kappa_2)^5$ or $(\mu_2\lambda_2)^5$
    (mmunoglobulin D(IgD)
        or $\gamma$D-Globulin ($\gamma$D)
    Mol. formula:
        $(\delta_2\kappa_2)$ or $(\delta_2\lambda_2)$
    Immunoglobulin E (IgE)
        or $\gamma$E-Globulin ($\gamma$E)
    Mol. formula:
        $(\epsilon_2\kappa_2)$ or $(\epsilon_2\lambda_2)$
    Free $\kappa$ and $\lambda$ light chains
    Complement factors:
        C'1
            C'1q
            C'1r
            C'1s
        C'2
        C'3
            $\beta_1$A
            $\alpha_2$D
        C'4
        C'5
        C'6
        C'7
        C'8
        C'9

Important blood clotting factors include:

| BLOOD CLOTTING FACTORS | |
| --- | --- |
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, |

| BLOOD CLOTTING FACTORS | |
|---|---|
| International designation | Name |
| | plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone
  (parathromone)
Thyrocalcitonin
Insulin
Glucagon
Relaxin
Erythropoietin
Melanotropin
  (melanocyte-stimulating hormone; intermedin)
Somatotropin
  (growth hormone)
Corticotropin
  (adrenocorticotropic hormone)
Thyrotropin
Follicle-stimulating hormone
Luteinizing hormone
  (interstitial cell-stimulating hormone)
Luteomammotropic hormone
  (luteotropin, prolactin)
Gonadotropin
  (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF)
  CRF, LRF, TRF, Somatotropin-RF, GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrheae | Polysaccharide |
| Corynebacterium diphtheriae | Polysaccharide |
| Actinobacillus mallei; | Crude extract |
| Actinobacillus whitemori | |
| Francisella tularensis | Lipopolysaccharide |
| | Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and turberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; | Polysaccharide |
| Salmonella derby | |
| Salmonella pullorum | |
| Shigella dysenteriae | Polysaccharide |
| Shigella flexneri | |
| Shigella sonnei | Crude, Polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria
  Corynebacterium diptheriae
Pneumococci
  Diplococcus pneumoniae
Streptococci
  Streptococcus pyogenes
  Streptococcus salivarus
Staphylococci
  Staphylococcus aureus
  Staphylococcus albus
Neisseriae
  Neisseria meningitidis
  Neisseria gonorrheae

| Enterobacteriaciae | |
|---|---|
| Escherichia coli | |
| Aerobacter aerogenes | } The coliform bacteria |
| Klebsiella pneumoniae | |
| Salmonella typhosa | |
| Salmonella choleraesuis | } The Salmonellae |
| Salmonella typhimurium | |
| Shigella dysenteriae | |
| Shigella schmitzii | |
| Shigella arabinotarda | |
| | } The Shigellae |
| Shigella flexneri | |
| Shigella boydii | |
| Shigella Sonnei | |
| Other enteric bacilli | |
| Proteus vulgaris | |
| Proteus mirabilis | } Proteus species |
| Proteus morgani | |
| Pseudomonas aeruginosa | |
| Alcaligenes faecalis | |

-continued

| Vibrio cholerae |
| --- |

Hemophilus-Pordetella group
  Hemophilus influenzae,
    *H. ducreyi*
    *H. hemophilus*
    *H. aegypticus*
    *H. parainfluenzae*
  *Bordetella pertussis*
Pasteurellae
  *Pasteurella pestis*
  *Pasteurella tulareusis*
Brucellae
  *Brucella melitensis*
  *Brucella abortus*
  *Brucella suis*
Aerobic Spore-forming Bacilli
  *Bacillus anthracis*
  *Bacillus subtilis*
  *Bacillus megaterium*
  *Bacillus cereus*
Anaerobic Spore-forming Bacilli
  *Clostridium botulinum*
  *Clostridium tetani*
  *Clostridium perfringens*
  *Clostridium novyi*
  *Clostridium septicum*
  *Clostridium histolyticum*
  *Clostridium tertium*
  *Clostridium bifermentans*
  *Clostridium sporogenes*
Mycobacteria
  *Mycobacterium tuberculosis hominis*
  *Mycobacterium bovis*
  *Mycobacterium avium*
  *Mycobacterium leprae*
  *Mycobacterium paratuberculosis*
Actinomycetes (fungus-like bacteria)
  *Actinomyces israelii*
  Actinomyces bovis
  Actinomyces naeslundii
  Nocardia asteroides
  Nocardia brasiliensis
The Spirochetes
  *Treponema pallidum*
  *Treponema pertenue*
  *Treponema carateum*
  *Borrelia recurrentis*
  *Leptospira icterohemorrhagiae*
  *Leptospira canicola*
  *Spirillum minus*
  *Streptobacillus moniliformis*
Mycoplasmas
  *Mycoplasma pneumoniae*
Other pathogens
  *Listeria monocytogenes*
  *Erysipelothrix rhusiopathiae*
  *Streptobacillus moniliformis*
  *Donvania granulomatis*
  *Bartonella bacilliformis*
Rickettsiae (bacteria-like parasites)
  *Rickettsia prowazekii*
  *Rickettsia mooseri*
  *Rickettsia rickettsii*
  *Rickettsia conori*
  *Rickettsia australis*
  *Rickettsia sibiricus*
  *Rickettsia akari*
  *Rickettsia tsutsugamushi*
  *Rickettsia burnetii*
  *Rickettsia quintana*
Chlamydia (unclassifiable parasites bacterial/viral)
  Chlamydia agents (naming uncertain)
Fungi
  *Cryptococcus neoformans*
  *Blastomyces dermatidis*
  *Histoplasma capsulatum*
  *Coccidioides immitis*
  *Paracoccidioides brasiliensis*
  *Candida albicans*
  *Aspergillus fumigatus*
  *Mucor corymbifer* (*Absidia corymbifera*)

| | |
| --- | --- |
| *Rhizopus oryzae* <br> *Rhizopus arrhizus* <br> *Rhizopus nigricans* | Phycomycetes |

*Sporotrichum schenkii*
  *Fonsecaea pedrosoi*
  *Fonsecaea compacta*
  *Fonsecaea dermatidis*
  *Cladosporium carrionii*
  *Phialophora verrucosa*
  *Aspergillus nidulans*
  *Madurella mycetomi*
  *Madurella grisea*
  *Allescheria boydii*
  *Phialosphora jeanselmei*
  *Microsporum gypseum*
  *Trichophyton mentagrophytes*
  *keratinomyces ajelloi*
  *Microsporum canis*
  *Trichophyton rubrum*
  *Microsporum andouini*
Viruses
  Adenoviruses
  Herpes Viruses
    *Herpes simplex*
    Varicella (Chicken pox)
    *Herpes Zoster* (Shingles)
    Virus B
    Cytomegalovirus
  Pox Viruses
    Variola (smallpox)
    Vaccinia
    *Poxvirus bovis*
    Paravaccinia
    *Molluscum contagiosum*
  Picornaviruses
    Poliovirus
    Coxsackievirus
    Echoviruses
    Rhinoviruses
  Myxoviruses
    Influenza (A, B, and C)
    Parainfluenza (1–4)
    Mumps Virus
    Newcastle Disease Virus
    Measles Virus
    Rinderpest Virus
    Canine Distemper Virus
    Respiratory Syncytial Virus
    Rubella Virus Arboviruses
  Eastern Equine Eucephalitis Virus
  Western Equine Eucephalitis Virus
  Sindbis Virus
  Chikugunya Virus
  Semliki Forest Virus
  Mayora Virus
  St. Louis Encephalitis Virus
  California Encephalitis Virus
  Colorado Tick Fever Virus
  Yellow Fever Virus
  Dengue Virus
Reoviruses
  Reovirus Types 1–3
Hepatitis
  Hepatitis A Virus
  Hepatitis B Virus
Tumor Viruses
  Rauscher Leukemia Virus
  Gross Virus
  Maloney Leukemia Virus The monoepitopic ligand analytes will generally be from about 100 to 2,000 molecular weight, more usually from 125 to 1,000 molecular weight. The analytes of interest include drugs, metabolites, pesticides, pollutants, and the like. Included amount of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids; their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steriod mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met-and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 6,000,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

Ligand Analog

The ligand analog will differ from the ligand either by replacement of a hydrogen or a functionality with a bond or a linking group which has a functionality for forming a covalent bond to another molecule having an active functionality, such as an hydroxyl, amino, aryl, thio, olefin, etc., where the resulting compound differs from the ligand by more than substitution of a hydrogen by the molecule to which it is conjugated. The linking group will normally have from 1–20 atoms other than hydrogen, which are carbon, oxygen, sulfur, nitrogen, and halogen of atomic number 17–35. The functionalities which are involved include carbonyl, both oxo and non-oxo, active halogen, diazo, mercapto, ethylene, particularly activated ethylene, amino, and the like. The number of heteroatoms will generally range from about 0–6, more usually from about 1–6, and preferably from about 1–4. A description of linking groups may be found in U.S. Pat. No. 3,817,837, which disclosure is incorporated herein by reference.

For the most part, the linking groups will be aliphatic, although with diazo groups, aromatic groups are involved. Generally, the linking group is a divalent chain having about 1–10, more usually from about 1–6 atoms in the chain. Oxygen will normally be present as oxo or oxy, bonded to carbon and hydrogen, preferably bonded solely to carbon, while nitrogen will normally be present as amino, bonded solely to carbon, or amido, while sulfur would be analogous to oxygen.

Common functionalities in forming the covalent bond between the linking group and the molecule to be conjugated are alkylamine, amide, amidine, thioamide, urea, thiourea, guanidine, and diazo.

Linking groups which find particular application with conjugation to polypeptides are those involving carboxylic acids which may be used in conjunction with diimides, or as mixed anhydrides with carbonate monoesters or as active carboxylic esters e.g. N-hydroxy succinimide or p-nitrophenyl. Nitrogen analogs may be employed as imidoesters. Aldehydes can be used to form imines under reductive amination conditions e.g. in the presence of borohydrides, to produce alkylamines. Other non-oxo carbonyl groups which may be employed include isocyanates and isothiocyanates. In addition, active halide may be employed, particularly bromoacetyl groups.

In most instances, the ligand will have one or more functional groups which may be employed as the site for linking the linking group. Particularly, hydroxy, amino and aryl groups, particularly activated aryl groups find use. Also, oximes may be prepared from oxo functionalities and the hydroxyl used as a site for joining to a linking group, such as carboxymethyl.

The choice of linking group will vary widely, depending upon the functionalities which are present in the ligand, in the compound to which the ligand is to be conjugated, the nature and length of the linking group desired, and the like.

Signal Producing System

The signal producing system will have at least one member and may have two or more members. The signal producing system provides for the production of a product which allows for a detectible signal in an amount or at a level related to the amount of analyte in a sample. The signal produced is normally on a solid support, so that the measurement will normally be from the solid support. The measurement will normally involve electromagnetic radiation absorption or emission.

A wide variety of different signal producing systems may be employed. Furthermore, as to each signal producing system, various members of the signal producing system may be employed as the signal label-mip conjugate or as signal label-support conjugate. In addition, the signal label-mip conjugate may be provided in solution or complexed to the mip-support conjugate.

The various conjugates may be joined covalently or non-covalently, direcly or indirectly. When bonded covalently, the particular linking group will depend upon the nature of the two moieties to be bonded and their respective functions. A large number of linking groups and methods for linking are taught in the literature. A significant number of linking groups are set forth in the section on ligand analogs.

Binding can also be achieved by the use of receptors. For instance, an antigen may be bound to a support through the intermediacy of a receptor e.g. antibody, for the antigen. The receptor in turn may be bound covalently or non-covalently e.g. adsorption to a support.

Arbitrarily, the signal producing systems will be divided into the following categories: chromogens; catalyzed reactions; chemiluminesence; and radioactive labels.

Chromogens

The chromogens will include compounds which absorb light in a distinctive range, so that a color may be observed, or emit light when irradiated with light of a particular wavelength or wavelength range e.g. fluorescers.

For the most part, the use of dyes as the signal label, which are measured by light absorption, will not provide for the desired sensitivity. While one can provide for a signal label involving a plurality of light absorptive functionalities, generally the concentration will be insufficient to provide a sufficient signal. However, by providing for a reasonable depth of immunobinding of signal label as well as a sufficient number of chromophoric functionalities bound to a mip, with a substantially transparent immunosorbing zone, it is feasible to employ dyes absorbing light in the visual region as the signal label.

One could greatly enhance the sensitivity of the system by employing soluble hub nuclei to which a plurality of ligands and signal labels are bound. Since the subject system allows for an extremely thorough washing of the immunosorbing zone, background values can be minimized.

The choice of dye may be varied widely, being primarily chosen to provide an intense color with minimum absorption by the immunosorbing zone support. Illustrative dye types include quinoline dyes, triarylmethane dyes, acridine dyes, alizarin dyes, phthaleins, insect dyes, azo dyes, anthraquinoid dyes, cyanine dyes, phenazathionium dyes, and phenazoxonium dyes.

A wide variety of fluorescers may be employed either by themselves or in conjunction with quencher molecules.

Fluorescers of interest fall into a variety of categories having certain primary functionalities. These primary functionalities include 1- and 2-aminoaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthene, 7-hydroxycoumarin, phenoxazine, salicylate, strophanthidin, porphyrins, triarylmethanes and flavin.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2-aminonaphthalene-6-sulfonate, ethidium bromide, atebrine, auromine-0, 2-(9'-anthroyl)palmitate, dansyl phosphatidylethanolamine, N,N'-dioctadecyl oxacarbocyanine, N,N'-dihexyl oxacarbocyanine, merocyanine, 4-(3'-pyrenyl)butyrate, d-3-aminodesoxyequilenin, 12-(9'-anthroyl)stearate, 2-methylanthracene, 9-vinylanthracene, 2,2'-(vinylene-p-phenylene)-bis-benzoxazole, p-bis[2-(4-methyl-5-phenyloxazolyl)]benzene, 6-dimethylamino-1,2-benzophenazin, retinol, bis(3'- aminopyridinium) 1,10-decandiyl diiodide, sulfonaphthylhydrazone of hellebrigenin, chlortetracycline, N-(7-dimethylamino-4-methyl-2-oxo-3-chromenyl) maleimide, N-[p-(2-benzimidazolyl)-phenyl]maleimide, N-(4-fluoranthyl) maleimide, bis(homovanillic acid), resazarin, 4-chloro-7-nitro-2.1.3-benzooxadiazole, merocyanine 540, resorufin, rose bengal, and 2,4-diphenyl-3(2H)-furanone.

Desirably fluorescers should absorb light above about 300 nm, preferably above 350 nm and more preferably above about 400 nm, usually emitting at wavelengths greater than 10 nm higher than the wavelength of the light absorbed. The primary concern is that proteins present in the immunosorbing zone do not interfere.

It should be noted that the absorption and emission characteristics of the bound dye may differ from the unbound dye. Therefore, when referring to the various wavelength ranges and characteristics of the dyes, it is intended to indicate the dyes as employed and not the dye which is unconjugated and characterized in an arbitrary solvent.

Fluorescers are preferred to absorptive dyes to the extent that a single fluorescer can provide for multiplication of a signal. By irradiating a fluorescer with light, one can obtain a plurality of emissions. Thus, a single label can provide for a plurality of measurable events.

Various other combinations and protocols could be employed depending upon the nature of the analyte.

Catalysis

As already indicated, both enzymatic and nonenzymatic catalysts may be employed. Preferably, enzymatic catalysts will be employed, since they frequently provide for more rapid reactions, a desirable versatility in the variety of reactions, and have well characterized properties.

In choosing an enzyme, there will be many considerations in addition to those involved with the reaction of interest. These considerations include the stability of the enzyme, the desirability of a high turnover rate, the sensitivity of the rate to variations in the physical environment, the nature of the substrate(s) and product(s), the availability of the enzyme, the effect of conjugation of the enzyme on the enzyme's properties.

The following are categories of enzymes as set forth in accordance with the classification of the International Union of Biochemistry.

TABLE II

1. Oxiodoreductases
    1.1 Acting on the CH—OH group of donors
        1.1.1 With NAD or NADP as acceptor
        1.1.2 With a cytochrome as an acceptor
        1.1.3 With $O_2$ as acceptor
        1.1.99 With other acceptors
    1.2 Acting on the aldehyde or keto group of donors
        1.2.1 With NAD or NADP as acceptor
        1.2.2 With cytochrome as an acceptor
        1.2.3 With $O_2$ as acceptor
        1.2.4 With lipoate as acceptor
        1.2.99 With other acceptors
    1.3 Acting on the CH—CH group of donors
        1.3.1 With NAD or NADP as acceptors
        1.3.2 With a cytochrome as an acceptor
        1.3.3 With $O_2$ as acceptor
        1.3.99 With other acceptors
    1.4 Acting on the CH—$NH_2$ group of donors
        1.4.1 With NAD or NADP as acceptor
        1.4.3 With $O_2$ as acceptor
    1.5 Acting on the C—NH group of donors
        1.5.1 With NAD or NADP as acceptor
        1.5.3 With $O_2$ as acceptor
    1.6 Acting on reduced NAD or NADP as donor
        1.6.1 With NAD or NADP as acceptor
        1.6.2 With a cytochrome as an acceptor
        1.6.4 With a disulfide compound as acceptor
        1.6.5 With a quinone or related compound as acceptor
        1.6.6 With a nitrogenous group as acceptor
        1.6.99 With other acceptors
    1.7 Acting on other nitrogeneous compounds as donors
        1.7.3 With $O_2$ as acceptor
        1.7.99 With other acceptors
    1.8 Acting on sulfur groups of donors
        1.8.1 With NAD or NADP as acceptor
        1.8.3 With $O_2$ as acceptor
        1.8.4 With a disulfide compound as acceptor
        1.8.5 With a quinone or related compound as acceptor
        1.8.6 With nitrogeneous group as acceptor
    1.9 Acting on heme groups of donors
        1.9.3 With $O_2$ as acceptor
        1.9.6 With a nitrogeneous group as acceptor
    1.10 Acting on diphenols and related substances as donors
        1.10.3 With $O_2$ as acceptors
    1.11 Acting on $H_2O_2$ as acceptor
    1.12 Acting on hydrogen as donor
    1.13 Acting on single donors with incorporation of oxygen (oxygenases)
    1.14 Acting on paired donors with incorporation of oxygen into one donor (hydroxylases)
        1.14.1 Using reduced NAD or NADP as one donor
        1.14.2 Using ascorbate as one donor
        1.14.3 Using reduced pteridine as one donor
2. Transferases
    2.1 Transferring one-carbon groups
        2.1.1 Methyltransferases
        2.1.2 Hydroxymethyl-, formyl- and related transferases
        2.1.3 Carboxyl- and carbamoyltransferases
        2.1.4 Amidinotransferases
    2.2 Transferring aldehydic or ketonic residues
    2.3 Acyltransferases
        2.3.1 Acyltransferases
        2.3.2 Aminoacyltransferases
    2.4 Glycosyltransferases
        2.4.1 Hexosyltransferases
        2.4.2 Pentosyltransferases
    2.5 Transferring alkyl or related groups
    2.6 Transferring nitrogenous groups
        2.6.1 Aminotransferases
        2.6.3 Oximinotransferases
    2.7 Transferring phosphorus-containing groups
        2.7.1 Phosphotransferases with an alcohol group as acceptor
        2.7.2 Phosphotransferases with a carboxyl group as acceptor
        2.7.3 Phosphotransferases with a nitrogeneous group as acceptor
        2.7.4 Phosphotransferases with a phospho-group as acceptor
        2.7.5 Phosphotransferases, apparently intromolecular 2.7.6 Pyrophosphotransferases
2.7.7 Nucleotidyltransferases
2.7.8 Transferases for other substituted phospho-groups
2.8 Transferring sulfur-containing groups
  2.8.1 Sulfurtransferases
  2.8.2 Sulfotransferases
  2.8.3 CoA-transferases
3. Hydrolases
  3.1 Acting on ester bonds
    3.1.1 Carboxylic ester hydrolases
    3.1.2 Thiolester hydrolases
    3.1.3 Phosphoric monoester hydrolases
    3.1.4 Phosphoric diester hydrolases
    3.1.5 Triphosphoric monoester hydrolases
    3.1.6 Sulfuric ester hydrolases
  3.2 Acting on glycosyl compounds
    3.2.1 Glycoside hydrolases
    3.2.2 Hydrolyzing N-glycosyl compounds
    3.2.3 Hydrolizing S-glycosyl compounds
  3.3 Acting on ether bonds
    3.3.1 Thioether hydrolases
  3.4 Acting on peptide bonds (peptide hydrolases)
    3.4.1 α-Aminoacyl-peptide hydrolases
    3.4.2 Peptidyl-aminoacid hydrolases
    3.4.3 Dipeptide hydrolases
    3.4.4 Peptidyl-peptide hydrolases
  3.5 Acting on C—N bonds other than peptide bonds
    3.5.1 In linear amides
    3.5.2 In cyclic amides
    3.5.3 In linear amidines
    3.5.4 In cyclic amidines
    3.5.5 In cyanides
    3.5.99 In other compounds
  3.6 Acting on acid-anhydride bonds
    3.6.1 In phosphoryl-containing anhydrides
  3.7 Acting on C—C bonds
    3.7.1 In ketonic substances
  3.8 Acting on halide bonds
    3.8.1 In C-halide compounds
    3.8.2 In P-halide compounds
  3.9 Acting on P—N bonds
4. Lyases
  4.1 Carbon-carbon lyases
    4.1.1 Carboxy-lysases
    4.1.2 Aldehyde-lyases
    4.1.3 Ketoacid-lyases
  4.2 Carbon-oxygen lyases
    4.2.1 Hydro-lyases
    4.2.99 Other carbon-oxygen lyases
  4.3 Carbon-nitrogen lyases
    4.3.1 Ammonia-lyases
    4.3.2 Amidine-lyases
  4.4 Carbon-sulfur lyases
  4.5 Carbon-halide lyases
  4.99 Other lyases
5. Isomerases
  5.1 Racemases and epimerases
    5.1.1 Acting on amino acids and derivatives
    5.1.2 Acting on hydroxy acids and derivatives
    5.1.3 Acting on carbohydrates and derivatives
    5.1.99 Acting on other compounds
  5.2 Cis-trans isomerases
  5.3 Intramolecular oxidoreductases
    5.3.1 Interconverting aldoses and ketoses
    5.3.2 Interconverting keto and enol groups
    5.3.3 Transposing C=C bonds
  5.4 Intramolecular transferases
    5.4.1 Transferring acyl groups
    5.4.2 Transferring phosphoryl groups
    5.4.99 Transferring other groups
  5.5 Intramolecular lyases
  5.99 Other isomerases
6. Ligases or Synthetases
  6.1 Forming C—O bonds
    6.1.1 Aminoacid-RNA ligases
  6.2 Forming C—S bonds
    6.2.1 Acid-thiol ligases
  6.3 Forming C—N bonds
    6.3.1 Acid-ammonia ligases (amide synthetases)
    6.3.2 Acid-aminoacid ligases (peptide synthetases)
    6.3.3 Cylo-ligases
    6.3.4 Other C—N ligases
    6.3.5 C—N ligases with glutamine as N-donor
  6.4 Forming C—C bonds Of particular interest will be enzymes which are in Class 1. Oxidoreductases and Class 3 hydrolases, although enzymes of Class 2, Transferases, Class 4 Lyases and Class 5, Isomerases, can also be of interest in particular situations.

The following table has specific subclasses of enzymes and specific enzymes within the subclass which are of particular interest. Among the oxidoreductases, those involving NAD or NADP, oxygen or hydrogen peroxide are of particular interest. Among the hydrolases, those involving phosphate and glycosides are of particular interest.

TABLE III

1. Oxidoreductases
  1.1 Acting on the CH—OH group of donors
    1.1.1 With NAD or NADP as acceptor
      1. alcohol dehydrogenase
      6. glycerol dehydrogenase
      27. lactate dehydrogenase
      37. malate dehydrogenase
      49. glucose-6-phosphate dehydrogenase
    1.1.3 With $O_2$ as acceptor
      4. glucose oxidase
      galactose oxidase
  1.2 Acting on the aldehyde or keto group of donors
    1.2.1 With NAD or NADP as acceptor
      12. glyceraldehyde-3-phosphate dehydrogenase
    1.2.3 With $O_2$ as acceptor
      2. xanthine oxidase
      luciferase
  1.4 Acting on the CH—$NH_2$ group of donors
    1.4.3 With $O_2$ as acceptor
      2. L-amino acid oxidase
      3. D-amino acid oxidase
  1.6 Acting on reduced NAD or NADP as donor
    1.6.99 With other acceptors
      diaphorase
  1.7 Acting on other nitrogeneous compounds as donors
    1.7.3 With $O_2$ as acceptor
      3. Uricase
  1.11 Acting on $H_2O_2$ as acceptor
    1.11.1
      6. catalase
      7. peroxidase
2. Transferases
  2.7 Transferring phosphorus-containing groups
    2.7.1 Phosphotransferases with CH—OH as acceptor 1. hexokinase
2. glucokinase
15. ribokinase
28. triokinase
40. pyruvate kinase
2.7.5
1. phosphoglucomutase
3. Hydrolases
3.1 Acting on ester bonds
3.1.1 Carboxylic ester hydrolases
7. cholinesterase
8. psuedo cholinesterase
3.1.3 Phosphoric monoester hydrolases
1. alkaline phosphatase
2. acid phosphatase
9. glucose-6-phosphatase
11. fructose diphosphatase
3.1.4 Phosphoric diester hydrolases
1. phosphodiesterase
3. phospholipase C
3.2 Acting on glycosyl compounds
3.2.1 Glycoside hydrolases
1. alpha amylase
2. beta amylase
4. cellulase
17. muramidase
18. neuraminidase
21. beta glucosidase
23. beta galactosidase
31. beta glucuronidase
35. hyaluronidase
3.2.2 Hydrolyzing N-glycosyl compounds
5. DPNase
4. Lyases
4.1 Carbon-carbon lyases
4.1.2 Aldehyde lyases
13. aldolyase
4.2.1 Hydro-lyases
1. carbonic anhydrase
5. Isomerase
5.4 Intramolecular transferases
5.4.2 Transferring phosphoryl group triose phosphate isomerase Of particular interest in the subject invention is the use of coupled catalysts, usually two or more enzymes, where the product of one enzyme serves as the substrate of the other enzyme. One or more enzymes are bound to the surface, while one enzyme is always bound to a mip. Alternatively, two enzymes can be bound to a mip and an additional enzyme may be bound to the surface.

The solute will be the substrate of any one of the enzymes, but preferably of an enzyme bound to the surface. The enzymatic reaction may involve modifying the solute to a product which is the substrate of another enzyme or production of a compound which does not include a substantial portion of the solute, which serves as an enzyme substrate. The first situation may be illustrated by glucose-6-phosphate being catalytically hydrolyzed by alkaline phosphatase to glucose, wherein glucose is a substrate for glucose oxidase. The second situation may be illustrated by glucose formed from glucose-6-phosphate being oxidized by glucose oxidase to provide hydrogen peroxide which would enzymatically react with the signal generator precursor and a peroxide to produce the signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. For example, G6PDH could catalyze the conversion of NAD and G6P to NADH which reacts with tetrazolium salts to produce an insoluble dye.

A wide variety of nonenzymatic catalysts which may be employed in this invention are found in U.S. Pat. No. 4,160,645, the appropriate portions of which are incorporated herein by reference. The nonenzymatic catalysts employ as reactants a first compound which reacts by a 1-electron transfer and a second compound which reacts by a 2-electron transfer, where the two reactants are capable of reacting with each other slowly, if at all, in the absence of the catalyst.

Various combinations of enzymes may be employed to provide a signal generating compound at the surface. Particularly, combinations of hydrolases may be employed to produce an insoluble signal generator. A single hydrolase may act in a substantially equivalent manner to an enzyme pair by employing the appropriate substrate. Alternatively, combinations of hydrolases and oxidoreductases can provide the signal generator. Also, combinations of oxidoreductases may be used to produce an insoluble signal generator. The following table is illustrative of various combinations which may be employed to provide for preferential production of the signal generating compound at the surface. Usually there will be a preferred catalyst at the surface, since as indicated previously, by appropriate choice of the catalyst at the surface, a greater number of reagents may be combined in a single formulation.

In the following table the first enzyme is intended to be bound to the surface and the second enzyme to a mip, although in particular situations it may be desirable to reverse their positions.

| INTERRELATED TWO ENZYME SYSTEMS | | | |
|---|---|---|---|
| First Enzyme | Second Enzyme | Solute | Signal Generation |
| 1. Galactose oxidase | horse radish peroxidase | β-D-galactose | 4-Cl—1-naphthol dye |
| 2. uricase | horse radish peroxidase | urate | o-dianisidine dye |
| 3. glucose oxidase | microperoxidase | β-D-glucose | bis-toluidine dye |
| 4. esterase | β-glucuronidase | 2,2-bis(3'-chloro-4'-glucuronyloxyphenyl) phthalide choline chloride ester | 3',3''-dichlorophenolphthalein |
| 5. alkaline phosphatase | peroxidase | 4-Cl—1-naphthyl phosphate | 4-Cl—1-naphthol dye |
| 6. hexokinase | glucose-6-phosphate dehydrogenase | glucose | iodonitrotriphenyl formazan |
| 7. alkaline phosphatase | β-galactosidase | $O^7$—(β-D-galactosidyl-6'-phosphate) 4-alkylumbelliferone | 4-alkylumbelliferone |

| First Enzyme | Reactions |
|---|---|
| 1. Galactose oxidase | 1. galactose + $O_2 \rightarrow$ D-galactono-δ-lactone + $H_2O_2$ |
| | 2. $H_2O_2$ + 4-Cl—1-naphthol $\rightarrow$ dye |
| 2. uricase | 1. urate + $O_2 \rightarrow$ allantoin + $H_2O_2$ |
| | 2. $H_2O_2$ + o-dianisidine $\rightarrow$ dye |
| 3. glucose | 1. glucose + $O_2 \rightarrow$ D-glucono-δ-lactone |

-continued

INTERRELATED TWO ENZYME SYSTEMS

| | | |
|---|---|---|
| | oxidase | + $H_2O_2$ |
| | | 2. $H_2O_2$ + bis-toluidine→dye |
| 4. | esterase | 1. 2,2-bis(3'-chloro-4'-glucuronyloxyphenyl) phthalide choline chloride→2,2-bis (3'-chloro-4'-glucuronyloxyphenyl)-phthalide |
| | | 2. 2,2-bis(3'-chloro-4'-glucuronyloxy-phenyl)phthalide→3',3''-dichloro-phenolphthalein |
| 5. | alkaline phosphatase | 1. 4-Cl—1-naphthyl phosphate→4-Cl—1-naphthol |
| | | 2. 4-Cl—1-naphthol→dye |
| 6. | hexokinase | 1. glucose + ATP→glucose-6-phosphate |
| | | 2. glucose-6-phosphate + NADP→NADPH phenazine methosulfate + NADPH + triphenyltetrazolium chloride→formazan |
| 7. | alkaline phosphate | 1. $O^7$—($\beta$-D-galactosidyl-6'-phosphate)-4-alkylumbelliferone→$O^7$—($\beta$-D-galactosidyl) 4-alkylumbelliferone |
| | | 2. $O^7$—($\beta$-D-galactosidyl)4-alkylumbel-liferone→4-alkylumbelliferone |

INTERRELATED ENZYME AND NON-ENZYMATIC CATALYST SYSTEMS

| Enzyme on mip | Catalyst | Solute | Signal Generation* |
|---|---|---|---|
| 1. G-6-PDH | Meldola blue | NAD | formazan |
| 2. lactate dehydrogenase | phenazine methosulfate | NAD | benzyl-viologen dye |
| 3. 3-hydroxy butyrate dehydrogenase | pyocyanine | NAD | formazan |

| Enzyme on mip | Reactions |
|---|---|
| 1. G-6-PDH | 1. G-6-P + NAD→ glucuronate-6-P + NADH |
| | 2. NADH + triphenyltetrazolium→NAD + formazan |
| 2. lactate dehydrogenase | 1. lactate + NAD→pyruvate + NADH |
| | 2. NADH + benzyl viologen→NAD + dye |
| 3. 3-hydroxy butyrate dehydrogenase | 1. 3-hydroxybutyrate + NAD→acetoacetate + NADH |
| | 2. NADH + triphenyltetrazolium→NAD + formazan |

*Precursor to signal generator may be covalently bonded to solid surface.

Quite obviously, many of the dyes indicated above may be substituted with other dyes which have the proper solubility requirements or which can be modified to have the proper solubility requirements for the subject invention. In addition, it should be appreciated, that by having a high localized concentration of the dye, the dye will have a tendency to bind to the surface. In addition, any incremental amount of dye which diffuses from the bulk solution to the surface will not significantly affect the amount of dye which precipitates on the surface. Depending upon the nature of the dye, either light absorption by the dye or, if fluorescent, light emission may be measured. Instead of dyes, electroactive compounds may be produced and electrical properties at the surface measured.

Various techniques can be employed to generate a signal in the detection zone. For example, the environment of the signal generator can be selectively modified, upon binding to the surface, so as to provide a detectible signal. For example, one could hydrolyze an ester or ether to produce an insoluble pH sensitive dye at the surface. The local pH at the surface will be made substantially different from the bulk solution by having charged groups on the surface. By employing a signal generating compound which is sensitive to proton concentration, the observed signal from the product bound to the surface would differ greatly from the product in the bulk solution or liquid phase. Fluorescer-quencher pairs may also be employed where the solute produces an insoluble quencher molecule, which binds to the surface. Increasing amounts of the quencher molecule on the surface will result in substantially decreased fluorescence from the fluorescent molecules bonded to the surface.

As an alternative to employing an enzyme as a signal label, one may employ a substrate as a signal label. However, in most instances, where a substrate (including co-factor) is the signal label of the signal label-mip conjugate, there will not be a high degree of amplification. Nevertheless, in some instances, this may be satisfactory. For example, various chromogens, particularly fluorescers, may be modified by an enzymatically labile functionality which results in a product which is non-fluorescent. For example, phosphate esters or glycosidyl ethers of phenolic fluorogens e.g. umbelliferone or fluorescein, may be prepared which are non-fluorogenic. However, upon enzymatic cleavage of the ester or ether bond with, for example, alkaline phosphatase or glycosidase, the resulting product would be fluorescent. In this mode, the enzyme would be a reagent provided in the reagent solution for developing the signal generator compound.

Where a co-factor is employed, desirably the co-factor would be cycled producing a chromogenic product which would precipitate on the surface. This type of reaction has been described above.

Chemiluminescers

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters e.g. p-nitrophenyl and a peroxide e.g. hydrogen peroxide, under basic conditions. Alternatively, luciferins may be used in conjunction with luciferase or lucigenins.

Radioactive Levels

Various radioisotope find common use. These include tritium ($^3H$), radioactive iodine ($^{125}I$), radioactive carbon ($^{14}C$), radioactive phosphorus ($^{32}P$); or the like.

Methods for labeling of compounds with radioactive labels are well known in the art.

Ancillary Materials

Various ancillary materials will frequently be employed in the subject assays. Particularly, enzyme substrates, co-factors, activators, unlabelled mips, or the like may be included in the assay medium.

In addition, buffers will normally be present, as well as stabilizers. Frequently in addition to these additives, additional proteins may be included, such as albumins; or surfactants, particularly non-ionic surfactants e.g. polyalkylene glycols, or the like.

Compositions

For performing the subject assays, assay devices and compositions will be provided, which will be selected to provide for maximizing the sensitivity of the assay.

Where the signal label-mip conjugate is not initially bound to the assay device, the reagent solution will normally include the signal label-mip conjugate. In addition to the aforementioned conjugate, other materials will be involved as appropriate. Desirably, the amount of reagents will be premeasured so that upon performing the assay, accurate measurements will not be required.

EXPERIMENTAL

The following examples are offered by way of illustration and not by way of limitation.

All percents and parts not otherwise indicated are by weight, except for mixtures of liquid which are by volume. When a solvent is not indicated, water is intended. All temperatures not otherwise indicated are Celsius. The following abbreviations are employed:

CMM—$O^3$-carboxymethyl morphine; HRP—horseradish peroxidase; NHS—N-hydroxy succinimide; DMF—N,N-dimethylformamide; THF—tetrahydrofuran; BSA—bovine serum albumin; HIgG—human immunoglobulin G; RT—room temperature; GO—glucose oxidase; EDCI—N-ethyl N-3-dimethylaminopropyl carbodiimide; SS—Schlesicher and Schnell.

EXAMPLE 1

Morphine-Horseradish Peroxidase (HRP) Conjugate

Into a reaction flask was combined 10$\mu$ moles $O^3$-carboxymethylmorphine, 11$\mu$ moles of N-hydroxy succinimide and 12$\mu$ moles of EDCI in a total volume of about 1.2 ml in DMF. After combining the reagents, the mixture was flushed with nitrogen and stirred overnight in a cold room. To 0.5 ml HRP (2 mg) in 50 mM aqueous sodium carbonate (pH 9.5) was added 150 ml DMF, followed by 300 $\mu$l of the above ester solution and the mixture allowed to stand overnight at 4°. The reaction mixture was then applied to a 2×30 cm column of G50 Sephadex and eluted with 0.1 M phosphate, pH 7.6, 0.1 M KCl and the protein monitored. The fractions in the void volume were pooled to provide 5.0 ml having a concentration of 0.2 mg/ml. By employing a radioactive tracer, the morphine/HRP molar ratio was found to be 1.86 with a concentration of HRP of 200 $\mu$g/ml.

EXAMPLE 2

Protein Coupling to Paper Filter Disk-Morphine

The following is the exemplary protocol employed for protein coupling to a paper support. SS 589 black ribbon filter paper disks, 0.193 mm thick, 12.5 cm dia. were activated in 0.1 M sodium periodate for 5 hrs. at room temperature. After washing with water extensively, 2 ml of the appropriate protein solution in 0.55 M borate, pH 8.5, 0.2 M NaCl, was added to the disks and the mixture allowed to stand for 2 hours at room temperature. To the mixture was then added 3.0 ml of a 1 mg/ml NaBH$_4$ solution and the mixture allowed to stand for 3 hrs. at room temperature, followed by termination by extensively washing the disks in 0.055 M borate, pH 8.5, with 0.2 M NaCl. The amount of protein bound to the disk was determined by a radiolabeled tracer.

The total protein coupled to the disk was 18.2 $\mu$g/cm$^2$.

An assay device was prepared employing a strip of SS470 paper, 0.895 mm thick, wide by 3.5 cm long and a 3/16" dia. disk, prepared as described previously, positioned at one end of the strip. The strip was then covered with Scotch ® tape to prevent any contact with solutions, except for an opening over the disk. Sample solutions were prepared having varying concentrations of morphine in synthetic urine (see infra, Table V). The device was dipped into the sample and remained there for 30 secs., during which time the solvent front had risen 3 cm. The device was then removed and dipped into a development solution containing 6 $\mu$l of a 1:100 diluted HRP-morphine conjugate, prepared as described above, per ml of a 0.05 M glucose, 200 $\mu$g/ml 4-Cl-1-naphthol solution, buffered to pH 7.0 with 0.1 M phosphate, EDTA, and NaCl. The device was kept in the development solution for 3 mins., during which time the solvent front rose 0.5 cm.

The colors are determined by comparison with a color chart developed by repetitive dilution of the developed dye to provide a range of colors in distinguishable steps. The following, Table IV, indicates the morphine concentration and the color produced on the disk. The paper was produced employing a ratio of 3 mg antimorphine to 5 mg glucose oxidase. For comparison, a second solution was employed, where the concentration of the HRP-morphine conjugate was 25 $\mu$l/ml.

TABLE IV

| Morphine Conc. ng/ml | Color Chart Value | |
|---|---|---|
| | 6$\mu$l/ml HRP-M | 25$\mu$l/ml HRP-M |
| 0 | 13, 13 | 20 |
| 0.1 | 11, 12 | 16 |
| 0.3 | 10 | 16 |
| 1.0 | 8 | 15 |
| 3.0 | 7 | 14 |
| 10.0 | 6 | 13 |
| 30.0 | 3 | 11 |
| 100.0 | 2 | 10 |
| 300.0 | 2 | 8 |

It is evident from the above results, that one can obtain a substantial differentiation in value over an extremely short time between 0 ng/ml and 1 ng/ml. Furthermore, the dynamic range varies from about 0 ng/ml of morphine to about 300 ng/ml of morphine.

The next study involved comparing the results with varying immunosorbing zones and different matrices. In each case the assay device was a 3/16" circular disk to which antibody to morphine was bound as well as glucose oxidase in varying ratios placed on a highly absorbent ⅜" wide long strip and the assembly encased in a hydrophobic barrier with a ⅛" orofice over the disk. The amount of HRP-morphine conjugate was varied. The developer solution or signal producing system solution was 200 μg/ml 4-Cl-1-naphthol, 0.05 M glucose, pH 7.0 phosphate buffer was EDTA and NaCl. The solvent front of the sample rose 3 cm while the development solution solvent front rose an additional 0.5 cm.

The following table indicates the results.

TABLE V

| Matrix | 2:3 Ab$_M$:GO$^a$ 6μl HRP-M/ml$^b$ Time sec | | Color Chart | |
|---|---|---|---|---|
| | Sample | Develop | $-^d$ | $+^e$ |
| Urine | 55 | 180 | 10 | <1 |
| Water | 35 | 180 | 9 | <1 |
| Syn. Urine$^c$ | 35 | 180 | 10 | <1 |

| Matrix | 3:5 Ab$_M$:GO$^a$ 25μl HRP-M/ml$^b$ Color Chart | | Densitometer$^f$ | |
|---|---|---|---|---|
| | $-^d$ | $+^e$ | − | + |
| Urine | 13 | 4 | 13.8 | 6.1 |
| Water | — | — | — | — |
| Syn. Urine$^c$ | 10 | 1 | 11.2 | 4.0 |

$^a$ratio of mg Ab$_M$ to mg GO employed in producing paper.
$^b$concentration of solution of conjugate of Ex. 1.
$^c$synthetic urine - major components in human urine.
$^d$0 ng/ml morphine
$^e$100 ng/ml morphine
$^f$Densitometer - optical density.

In the following study, a fluorescent label was employed. A test strip device was prepared using the papers described previously, which was 9 cm long containing a liquid absorbing strip 3/16" wide. Adjacent one end was placed a ⅛" diameter disk bearing antimorphine. The disk was in uniform contact with the liquid absorbing strip. The entire assembly enclosed in a hydrophobic barrier, except for a 3/16" diameter opening above the antimorphine containing disk.

The protocol employed is as follows. The device is immersed into a sample containing either no or 5 μg/ml morphine and the solvent front allowed to rise 2 cm. The device is then removed from the sample solution and immersed in a solution of approximately 25 μg/ml of a fluoresceinmorphine conjugate in 0.1 M phosphate buffer, pH 7.0. The device is maintained in the reagent solution until the solvent front has moved an additional 3 cm. The device is then removed from the reagent solution and placed in a washing solution of 0.1 M phosphate, pH 7.0 and maintained in the wash solution until the solvent front has moved an additional 4 cm. The disks are then visualized under short wave ultraviolet light and a clear difference in fluorescence intensity was visually observed between samples having no morphine and samples having 5 μg/ml morphine.

In the next study, a radioactive label was employed using a device essentially as described above, except that a ⅛" liquid absorbing strip was employed, as well as a ⅛" opening. Two different procedures were employed, one involving competitive binding and the other involving sequential binding.

In the competitive binding technique, the device is immersed into a 1 ml sample containing 50 ng of $^3$H-morphine and varying concentrations of morphine: 0; 100 ng; and 2,000 ng. After the solvent front has moved 3 cm, the device is removed and immersed into 0.1 M phosphate, pH 7.0 wash solution with 0.2 M NaCl and maintained until the solvent front has moved up 4 cm. The disk is removed and placed in a tube containing 1 ml of 0.1 M glycine-HCl, pH 2.2. After shaking for 30 min., a 500 μl aliquot of the solution is dissolved into 10 ml of scintillation cocktail and read for 1 min. The results are in cpm, for 0 morphine 48861; for 100 ng morphine 18441; and for 2,000 ng morphine 1781.

In the sequential test, the device is immersed in a sample for a sufficient time for the solvent front to move up the strip 2 cm. The device is then removed from the sample and immersed in a solution containing 20 μl $^{125}$I-HRP-morphine/ml in 0.1 M phosphate buffer, pH 7.0 with 0.1% Triton X-101 and 0.2 M NaCl and maintained until the solvent front moves 3 cm. The device is then removed and immersed into 0.1 M phosphate buffer, pH 7.0 with 0.1% Triton X-101 and 0.2 M NaCl and maintained until the solvent front has moved 4 cm. The portion of the device having the disk is cut-out and read on a gamma counter for 1 min. The following are the results where the first number indicates the concentration of morphine in ng/ml and the second the cpm: 0, 7187; 100, 2690; 2,000, 1755. When the test was repeated, except that Triton was not included in the buffer, the results for 0, 100 and 2,000 ng/ml were 6240; 2717 and 2030 respectively.

It is evident from the above results that various matrices can be tested without interfering with the result. The result can be analyzed visually or by an apparatus such as a densitometer or scintillation counter. The results are rapidly obtained with sharp differentiation between 0 and as little as 100 ng/ml of morphine or less.

In accordance with the subject invention, a simple rapid technique is provided whereby ligands and their receptors may be qualitatively or quantitatively determined by employing various techniques. Protocols having various numbers of steps, including as few as one can be employed for a determination of an analyte. Furthermore, the number of reagent measurements can be minimized and means for measuring provided which can be readily employed by lay personnel.

Although the foregoing invention has been described in some detail by way of illustration and example for purposes of clarity of understanding, it will be obvious that certain changes and modifications may be practiced within the scope of the appended claims.

What is claimed is:

1. An immunoassay method for determining an analyte which is a member of an immunological pair, defined as a mip, consisting of ligand and its homologous antiligand, said method employing in combination as assay device and a signal producing system;

said assay device characterized by an immunosorbing zone comprising mip non-diffusively bound to at least a portion of a bibulous support serving as an inlet port for liquids into said device; and a liquid absorbing zone in liquid receiving relationship with said immunosorbing zone; and a signal producing system characterized by being capable of producing a detectible signal in said immunosorbing zone and having one component conjugated to a mip to provide a signal label-mip conjugate, wherein the amount of signal label producing said detectible signal in said immunosorbing zone is related to the amount of analyte;

said method comprising:

contacting said assay device in a predetermined order with: (a) a solution of a sample suspected of containing said analyte; and (b) a solution of components of said signal producing system other than components bound to said assay device, wherein said immunosorbing zone is immersed in said sample solution;

flowing said sample solution of substantially constant composition through said immunosorbing zone;

whereby said solutions migrate through said immunosorbing zone into said liquid absorbing zone resulting in an amount of signal label-mip conjugate becoming bound to said mip bound to said support in relation to the amount of analyte in said sample and affording production of a detectable signal in said immunosorbing zone; and determining said detectable signal.

2. A method according to claim 1, wherein said signal label-mip conjugate is contacted with said assay device in a solution not earlier than concurrently with said sample solution.

3. A method according to claim 2, wherein said solution of said sample and said solution of said signal label-mip conjugate are combined prior to contacting with said assay device, with the proviso that where no additional solution of components of said signal producing system is combined with said assay device, said assay device is contacted with a wash solution subsequent to contacting with said sample and signal label solution.

4. A method according to claim 2, wherein said assay device is contacted with said solution of said sample in a first step; said assay device is contacted with a solution of said signal label-mip conjugate in a second step; and said assay device is contacted with remaining components of said signal producing system in a third step.

5. A method according to claim 1, wherein said signal label-mip conjugate is bound to said mip in said immunosorbing zone, wherein one of the mips is a monoepitopic ligand.

6. A method according to claim 5, where said assay device is contacted with said solution of said sample in a first step, and said assay device is contacted with said solution of components of said signal producing system in a subsequent step.

7. A method according to claims 1, 2, or 5, wherein said signal label is a fluorescer.

8. A method according to claims 1, 2 or 5, wherein said signal label is a radioisotope.

9. A method according to claim 7, wherein said analyte is a monoepitopic ligand.

10. A method according to claim 7, wherein said analyte is an antigen ligand.

11. A method according to claims 1, 2 or 5, wherein said signal label is an enzyme.

12. A method according to claim 11, wherein said analyte is a monoepitopic ligand.

13. A method according to claim 11, wherein said analyte is an antigen ligand.

14. A method according to claims 1, 2 or 5, wherein said analyte is an immunoglobulin.

15. An immunoassay method for determining an analyte which is a member of an immunological pair, defined as a mip, consisting of ligand and its homologous antiligand, said method employing in combination an assay device and a signal producing system;

said assay device characterized by an immunosorbing zone comprising mip non-diffusively bound to at least a portion of a bibulous support serving as an inlet port for liquids into said device; and a liquid absorbing zone in liquid receiving relationship with said immunosorbing zone and at least partially enclosed to prohibit contact with liquids except through said immunosorbing zone;

said signal producing system characterized by being capable of producing a detectible signal in said immunosorbing zone and having (1) an enzyme as a signal label conjugated to a mip to provide an enzyme-mip conjugate, wherein the amount of enzyme producing said detectible signal in said immunosorbing zone is related to the amount of analyte, and (2) a signal generator precursor which is enzymatically transformed to a signal generator;

said method comprising:

contacting said assay device in a predetermined order with: (a) a solution of a sample suspected of containing said analyte; (b) a solution of enzyme-mip conjugate, except when said enzyme-mip conjugate is previously bound to said assay device through complexation with said mip bound to said support; and (c) a solution of a signal generator precursor, wherein said immunosorbing zone is substantially completely immersed in said sample solution;

flowing said sample solution having substantially constant composition through said immunosorbing zone;

whereby said solutions migrate through said immunosorbing zone into said liquid absorbing zone and said signal generator precursor is converted by said enzyme to a signal generator producing a detectible signal in said immunosorbing zone; and determining said detectable signal.

16. A method according to claim 15, wherein a second enzyme is non-diffusively bound in said immunosorbing zone, wherein the product from one enzyme is a substrate for the other enzyme.

17. A method according to claim 16, wherein said second enzyme produces a product which is a substrate of said enzyme-mip conjugate.

18. A method according to claim 16, wherein said enzyme-mip conjugate and said signal generator precursor are combined prior to combining with said assay device.

19. A method according to claim 16 or 17, wherein said mip is bound to only a portion of said support and said second enzyme and antienzyme for said enzyme-mip conjugate are bound in a detection zone in said immunosorbing zone downstream from said mip.

20. A method according to claims 16 or 17, wherein said second enzyme is glucose oxidase and said enzyme-mip conjugate is horseradish peroxidase.

21. A method according to claim 18 wherein said assay device is contacted with said solution of said sample in a first step, and said assay device is contacted with said combined enzyme-mip conjugate and signal generator precursor in a second step.

22. An immunoassay method for determining an analyte which is a member of an immunological pair, defined as a mip, consisting of ligand and its homologous antiligand, said method employing in combination an assay device and a signal producing system;

said assay device characterized by an immunosorbing zone comprising mip non-diffusively bound to a bibulous support serving as a inlet port for liquids into said device; and a liquid absorbing zone in liquid receiving relationship with said immunosorbing zone and at least partially enclosed to prohibit contact with liquids except through said immunosorbing zone;

said signal producing system characterized by being capable of producing a detectible signal in said immunosorbing zone and having a fluorescer as signal label conjugated to a mip to provide a fluorescer-mip conjugate, wherein the amount of fluorescer producing said detectible signal in said immunosorbing zone is related to the amount of analyte;

said method comprising: contacting said assay device in a predetermined order with: (a) a solution of a sample suspected of containing said analyte; (b) a solution of fluorescer-mip conjugate, except when said fluorescer-mip conjugate is bound to said assay device prior to combining with said sample solution; and (c) a wash solution, except when said fluorescer-mip conjugate is bound to said assay device prior to combining with said sample solution, whereby said solutions migrate through said immunosorbing zone into said liquid absorbing zone and said fluorescer-mip conjugate is bound in said immunosorbing zone in relation to the amount of analyte in said sample; and determining the fluorescence from said immunosorbing zone.

23. A method according to claim 22, wherein said fluorescer-mip conjugate is bound to said assay device before contacting with said sample solution.

24. A method according to claim 22, wherein said fluorescer-mip conjugate is combined with said assay device after said sample solution is combined with said assay device.

25. An assay device for performing immunoassays which comprises:
   an immunosorbing member comprising a member of an immunological pair, defined as a mip, non-diffusively bound to at least a portion of a bibulous support; and
   a liquid absorbing member comprising a bibulous material in liquid receiving relationship with said immunosorbing member and extending transversely therefrom, wherein at least the portion of said liquid absorbing member about said immunosorbing member is enclosed in an impermeable enclosure to inhibit contact with solutions except through said immunosorbing member and said immunosorbing member has a relatively small liquid holding capacity as compared to said liquid absorbing member.

26. An assay device according to claim 25, wherein said immunosorbing member and said liquid absorbing member are a single strip, said immunosorbing member being at the end of said single strip.

27. An assay device according to claim 25, wherein said immunosorbing member is a layer above a portion of said liquid absorbing member.

28. An assay device according to claims 25, 26, or 27, wherein bound to said bilbulous support is an enzyme.

29. An assay device according to claims 25, 26, or 27, wherein bound to said mip is a labeled form of the homologous mip, substantially saturating all of the binding sites of said mip bound to said support.

30. An assay device for performing immunoassay comprising:
   (1) an immunosorbing member;
   (2) a liquid absorbing member;
   (3) a non-permeable barrier;
   said immunosorbing member serving as a liquid entry port to said device and comprised of at least two zones; a first bibulous layer to which a member of an immunological pair, defined as mip, is non-diffusively bound, and a second zone between said bibulous member and said liquid absorbing member of different flow resistant characteristic from said bibulous layer;
   said liquid absorbing member comprised of a bibulous layer in liquid receiving relationship with said immunosorbing zone and extending transversely therefrom, wherein said immunosorbing member has relatively small liquid holding capacity as compared to said liquid absorbing member; and
   said non-permeable barrier comprising a non-permeable layer about said liquid absorbing and immunosorbing members to inhibit entry of liquid to said device except through said immunosorbing member.

31. An assay device according to claim 30, wherein said second zone is substantially non-resistive to liquid flow.

32. An immunoassay kit comprising an assay device according to claims 25, 26, 27, or 30 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

33. A kit according to claim 32, wherein said label is an enzyme and including in combination, an enzyme substrate capable of providing a fluorescent or visible light absorptive product.

34. A kit according to claim 33, wherein said labeled mip is radioactively labeled mip.

* * * * *

REEXAMINATION CERTIFICATE (934th)
United States Patent [19]

Tom et al.

[11] B1 4,366,241
[45] Certificate Issued Oct. 18, 1988

[54] CONCENTRATING ZONE METHOD IN HETEROGENEOUS IMMUNOASSAYS

[75] Inventors: Henry K. Tom, La Honda; Gerald L. Rowley, Cupertino, both of Calif.

[73] Assignee: Syva Company, Palo Alto, Calif.

Reexamination Request:
No. 90/001,179, Mar. 4, 1987

Reexamination Certificate for:
Patent No.: 4,366,241
Issued: Dec. 28, 1982
Appl. No.: 176,177
Filed: Aug. 7, 1980

[51] Int. Cl.[4] .................. G01N 33/54; G01N 33/16; C12Q 1/70
[52] U.S. Cl. .......................... 435/7; 435/5; 435/805; 435/810; 422/56; 424/1
[58] Field of Search ................ 435/7, 5, 805, 810, 435/180; 422/55, 56, 61; 23/230 B, 230 R; 436/807

[56] References Cited

U.S. PATENT DOCUMENTS

| | | | |
|---|---|---|---|
| Re. 31,006 | 8/1982 | Schuurs et al. | 435/7 |
| 3,615,222 | 10/1971 | Mead | 435/7 |
| 3,645,687 | 2/1972 | Nerenberg | 435/7 |
| 3,715,192 | 2/1973 | Wenz et al. | 435/7 |
| 3,723,064 | 3/1973 | Liotta | 436/66 |
| 3,825,410 | 7/1974 | Bagshawe | 435/7 |
| 3,843,324 | 10/1974 | Edelman et al. | 435/7 |
| 3,888,629 | 6/1975 | Bagshawe | 23/230 B |
| 3,896,217 | 7/1975 | Johnson | 424/1 |
| 3,966,897 | 6/1976 | Renn et al. | 436/515 |
| 4,039,652 | 8/1977 | Adams et al. | 436/505 |
| 4,053,284 | 10/1977 | Posch | 435/7 |
| 4,087,248 | 5/1978 | Miles | 23/230 B |
| 4,092,115 | 5/1978 | Rupe et al. | 436/125 |
| 4,098,876 | 7/1978 | Piasio et al. | 436/500 |
| 4,125,372 | 11/1978 | Kawai et al. | 435/7 |
| 4,138,474 | 2/1979 | Updike et al. | 424/1 |
| 4,153,675 | 5/1979 | Kleinerman | 424/8 |
| 4,180,383 | 12/1979 | Johnson | 422/61 |
| 4,193,983 | 3/1980 | Ullman et al. | 424/12 |
| 4,200,690 | 4/1980 | Root et al. | 435/7 |
| 4,201,763 | 5/1980 | Monthony et al. | 435/7 |
| 4,235,601 | 11/1980 | Deutsch et al. | 436/514 |
| 4,244,940 | 1/1981 | Jeong et al. | 424/1 |
| 4,246,339 | 1/1981 | Cole | 435/7 |
| 4,258,001 | 5/1981 | Pierce et al. | 435/7 |
| 4,277,560 | 7/1981 | Gray et al. | 435/7 |
| 4,305,924 | 12/1981 | Piasio et al. | 424/1 |
| 4,376,110 | 3/1983 | David et al. | 436/513 |
| 4,391,904 | 7/1983 | Litman et al. | 435/805 |
| 4,407,943 | 10/1983 | Cole | 435/7 |
| 4,424,279 | 1/1984 | Bohn et al. | 436/539 |
| 4,425,438 | 1/1984 | Bauman | 436/527 |
| 4,427,769 | 1/1984 | Adlercreutz et al. | 435/7 |

FOREIGN PATENT DOCUMENTS

| | | |
|---|---|---|
| 1348938 | 3/1974 | United Kingdom . |
| 1401297 | 7/1975 | United Kingdom . |
| 1401298 | 7/1975 | United Kingdom . |
| 2001172A | 1/1979 | United Kingdom . |
| 2008767A | 6/1979 | United Kingdom . |
| 2018986A | 10/1979 | United Kingdom . |
| 1564578 | 4/1980 | United Kingdom . |

OTHER PUBLICATIONS

Millipore Toxoplasma Antibody Test, No. PB 847. Millipore Corporation, Bedford, MA, copyright 1979.

*Primary Examiner*—Thomas G. Wiseman
*Assistant Examiner*—Robin Lyn Teskin

[57] ABSTRACT

Method and apparatus are provided for performing immunoassays employing a device comprising a relatively small test zone referred to as an immunosorbing zone, and a relatively large liquid absorbing zone in liquid receiving relationship with said immunosorbing zone. The immunosorbing zone includes a member of an immunological pair ("mip")—ligand and antiligand—bound to a support.

A signal producing system is employed in conjunction with said device having as one component a signal label bound to a mip. The signal producing system provides for production of a detectible signal in the immunosorbing zone in relation to the amount of analyte in a sample.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 15-24 is confirmed.

Claims 1, 25, 30 and 34 are determined to be patentable as amended.

Claims 2-14, 26-29, and 31-33, dependent on an amended claim are determined to be patentable.

New claims 35-91 are added and determined to be patentable.

1. An immunoassay method for determining an analyte which is a member of an immunological pair, defined as a mip, consisting of ligand and its homologous antiligand, said method employing in combination [as] *an* assay device and a signal producing system;
   said assay device characterized by an immunosorbing zone comprising mip non-diffusively bound to at least a portion of a bibulous support serving as an inlet port for liquids into said device; and a liquid absorbing zone in liquid receiving relationship with said immunosorbing zone; and
   a signal producing system characterized by being capable of producing a detectible signal in said immunosorbing zone and having one component conjugated to a mip to provide a signal label-mip conjugate, wherein the amount of signal label producing said detectible signal in said immunosorbing zone is related to the amount of analyte;
   said method comprising:
   contacting said assay device in a predetermined order with: (a) a solution of a sample suspected of containing said analyte; and (b) a solution of components of said signal producing system other than components bound to said assay device, wherein said immunosorbing zone is immersed in said sample solution;
   flowing said sample solution of substantially constant composition through said immunosorbing zone;
   whereby said solutions migrate through said immunosorbing zone into said liquid absorbing zone resulting in an amount of signal label-mip conjugate becoming bound to said mip bound to said support in relation to the amount of analyte in said sample and affording production of a detectable signal in said immunosorbing zone; and
   determining said detectable signal.

25. An assay device for performing immunoassays which comprises:
   an immunosorbing member comprising a member of an immunological pair, defined as a mip, non-diffusively bound to at least a portion of a bibulous support; and
   a liquid absorbing member comprising a bibulous material in *fixed* liquid receiving relationship *throughout the duration of said immunoassay* with said immunosorbing member and extending transversely therefrom, wherein at least the portion of said liquid absorbing member about said immunosorbing member is enclosed in an impermeable enclosure to inhibit contact with solutions except through said immunosorbing member and said immunosorbing member has a relatively small liquid holding capacity as compared to said liquid absorbing member.

30. An assay device for performing *an* immunoassay comprising:
   (1) an immunosorbing member;
   (2) a liquid absorbing member;
   (3) a non-permeable barrier;
   said immunosorbing member serving as a liquid entry port to said device and comprised of at least two zones; a first bibulous layer to which a member of an immunological pair, defined as mip, is non-diffusively bound, and a second zone between said bibulous member and said liquid absorbing member of different flow resistant characteristic from said bibulous layer;
   said liquid absorbing member comprised of a bibulous layer in *fixed* liquid receiving relationship *throughout the duration of said immunoassay* with said immunosorbing zone and extending transversely therefrom, wherein said immunosorbing member has relatively small liquid holding capacity as compared to said liquid absorbing member; and
   said non-permeable barrier comprising a non-permeable layer about said liquid absorbing and immunosorbing members to inhibit entry of liquid to said device except through said immunosorbing member.

34. A kit according to claim [33] *32*, wherein said labeled mip is radioactively labeled mip.

*35. An assay device for performing immunoassays which comprises: an immunosorbing member comprising a member of an immunological pair, defined as a mip, non-diffusively bound to at least a portion of a bibulous support; and*
   *a liquid absorbing member comprising a bibulous material in non-movable liquid receiving relationship with and abutting said immunosorbing member and extending transversely therefrom, wherein at least the portion of said liquid absorbing member about said immunosorbing member is enclosed in an impermeable enclosure to inhibit contact with solutions except through said immunosorbing member and said immunosorbing member has a relatively small liquid holding capacity as compared to said liquid absorbing member.*

*36. An assay device according to claim 35, wherein said immunosorbing member and said liquid absorbing member are a single strip, said immunosorbing member being at the end of said single strip.*

*37. An assay device according to claim 35, wherein said immunosorbing member is a layer above a portion of said liquid absorbing member.*

*38. An assay device according to claim 35 wherein bound to said bibulous support is an enzyme.*

*39. An assay device according to claim 36 wherein bound to said bibulous support is an enzyme.*

40. An assay device according to claim 37 wherein bound to said bibulous support is an enzyme.

41. An assay device according to claim 35 wherein bound to said mip is a labeled form of the homologous mip, substantially saturating all of the binding sites of said mip bound to said support.

42. An assay device according to claim 36 wherein bound to said mip is a labeled form of the homologous mip, substantially saturating all of the binding sites of said mip bound to said support.

43. An assay device according to claim 37 wherein bound to said mip is a labeled form of the homologous mip, substantially saturating all of the binding sites of said mip bound to said support.

44. An assay device for performing an immunoassay comprising:
   (1) an immunosorbing member;
   (2) a liquid absorbing member;
   (3) a non-permeable barrier;
   said immunosorbing member serving as a liquid entry port to said device and comprised of at least two zones; a first bibulous layer to which a member of an immunological pair, defined as a mip, is non-diffusively bound, and a second zone between said bibulous member and said liquid absorbing member of different flow resistant characteristic from said bibulous layer;
   said liquid absorbing member comprised of a bibulous layer in non-movable liquid receiving relationship with and abutting said immunosorbing member and extending transversely therefrom, wherein said immunosorbing member has relatively small liquid holding capacity as compared to said liquid absorbing member; and
   said non-permeable barrier comprising a non-permeable layer about said liquid absorbing and immunosorbing members to inhibit entry of liquid to said device except through said immunosorbing member.

45. An assay device according to claim 44, wherein said second zone is substantially non-resistive to liquid flow.

46. An immunoassay kit comprising an assay device according to claim 35 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

47. An immunoassay kit comprising an assay device according to claim 36 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

48. An immunoassay kit comprising an assay device according to claim 37 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

49. An immunoassay kit comprising an assay device according to claim 44 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

50. A kit according to claim 46 wherein said label is an enzyme and including in combination, an enzyme substrate capable of providing a fluorescent or visible light absorptive product.

51. A kit according to claim 50 wherein said labeled mip is radioactively labeled mip.

52. An assay device for performing immunoassays which comprises: an immunosorbing member comprising a member of an immunological pair, defined as a mip, non-diffusively bound to at least a portion of a bibulous support; and a liquid absorbing member comprising a bibulous material adapted throughout the duration of said immunoassay to continuously draw liquid through said immunosorbing member as liquid is applied thereto, wherein at least the portion of said liquid absorbing member about said immunosorbing member is enclosed in an impermeable enclosure to inhibit contact with solutions except through said immunosorbing member and said immunosorbing member has a relatively small liquid holding capacity as compared to said liquid absorbing member.

53. An assay device according to claim 52, wherein said immunosorbing member and said liquid absorbing member are a single strip, said immunosorbing member being at the end of said single strip.

54. An assay device according to claim 52, wherein said immunosorbing member is a layer above a portion of said liquid absorbing member.

55. An assay device according to claim 52 wherein bound to said bibulous support is an enzyme.

56. An assay device according to claim 53 wherein bound to said bibulous support is an enzyme.

57. An assay device according to claim 54 wherein bound to said bibulous support is an enzyme.

58. An assay device according to claim 52 wherein bound to said mip is a labeled form of the homologous mip, substantially saturating all of the binding sites of said mip bound to said support.

59. An assay device according to claim 53 wherein bound to said mip is a labeled form of the homologous mip, substantially saturating all of the binding sites of said mip bound to said support.

60. An assay device according to claim 54 wherein bound to said mip is a labeled form of the homologous mip, substantially saturating all of the binding sites of said mip bound to said support.

61. An assay device for performing an immunoassay comprising:
   (1) an immunosorbing member;
   (2) a liquid absorbing member;
   (3) a non-permeable barrier;
   said immunosorbing member serving as a liquid entry port to said device and comprised of at least two zones; a first bibulous layer to which a member of an immunological pair, defined as a mip, is non-diffusively bound, and a second zone between said bibulous member and said liquid absorbing member of different flow resistant characteristic from said bibulous layer;
   said liquid absorbing member comprised of a bibulous layer adapted throughout the duration of said immunoassay to continuously draw liquid through said immunosorbing member as liquid is applied thereto, wherein said immunosorbing member has relatively small liquid holding capacity as compared to said liquid absorbing member; and
   said non-permeable barrier comprising a non-permeable layer about said liquid absorbing and immunosorbing members to inhibit entry of liquid to said device except through said immunosorbing member.

62. An assay device according to claim 61, wherein said second zone is substantially non-resistive to liquid flow.

63. An immunoassay kit comprising an assay device according to claim 52 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

64. An immunoassay kit comprising an assay device according to claim 53 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

65. An immunoassay kit comprising an assay device according to claim 54 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

66. An immunoassay kit comprising an assay device according to claim 61 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

67. A kit according to claim 63 wherein said label is an enzyme and including in combination, an enzyme substrate capable of providing a fluorescent or visible light absorptive product.

68. A kit according to claim 67 wherein said labeled mip is radioactively labeled mip.

69. An assay device for performing immunoassays which comprises:
an immunosorbing member comprising a member of an immunological pair, defined as a mip, non-diffusively bound to at least a portion of a bibulous support; and
a liquid absorbing member comprising a bibulous material in fixed, non-movable liquid drawing and receiving relationship with said immunosorbing member and extending transversely therefrom, wherein at least a portion of said liquid absorbing member about said immunosorbing member is enclosed in an impermeable enclosure to inhibit contact with solutions except through said immunosorbing member and said immunosorbing member has a relatively small liquid holding capacity as compared to said liquid absorbing member.

70. An assay device according to claim 69 wherein said immunosorbing member and said liquid absorbing member are a single strip, said immunosorbing member being at the end of said single strip.

71. An assay device according to claim 69 wherein said immunosorbing member is a layer above a portion of said liquid absorbing member.

72. An assay device according to claim 69 wherein bound to said bibulous support is an enzyme.

73. An assay device according to claim 70 wherein bound to said bibulous support is an enzyme.

74. An assay device according to claim 71 wherein bound to said bibulous support is an enzyme.

75. An assay device according to claim 69 wherein bound to said mip is a labeled form of the homologous mip, substantially saturating all of the binding sites of said mip bound to said support.

76. An assay device according to claim 70 wherein bound to said mip is a labeled form of the homologous mip, substantially saturating all of the binding sites of said mip bound to said support.

77. An assay device according to claim 71 wherein bound to said mip is a labeled form of the homologous mip, substantially saturating all of the binding sites of said mip bound to said support.

78. An assay device for performing an immunoassay comprising:
(1) an immunosorbing member;
(2) a liquid absorbing member;
(3) a non-permeable barrier;
said immunosorbing member serving as a liquid entry port to said device and comprised of at least two zones; a first bibulous layer to which a member of an immunological pair, defined as mip, is non-diffusively bound, and a second zone between said bibulous member and said liquid absorbing member of different flow resistant characteristic from said bibulous layer;
said liquid absorbing member comprised of a bibulous layer in fixed, non-movable liquid drawing and receiving relationship with said immunosorbing zone and extending transversely therefrom, wherein said immunosorbing member has relatively small liquid holding capacity as compared to said liquid absorbing member; and
said non-permeable barrier comprising a non-permeable layer about said liquid absorbing and immunosorbing members to inhibit entry of liquid to said device except through said immunosorbing member.

79. An assay device according to claim 78 wherein said second zone is substantially non-resistive to liquid flow.

80. An immunoassay kit comprising an assay device according to claim 69 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

81. An immunoassay kit comprising an assay device according to claim 70 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

82. An immunoassay kit comprising an assay device according to claim 71 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

83. An immunoassay kit comprising an assay device according to claim 78 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

84. A kit according to claim 80 wherein said label is an enzyme and including in combination, an enzyme substrate capable of providing a fluorescent or visible light absorptive product.

85. A kit according to claim 84 wherein said labeled mip is radioactively labeled mip.

86. An assay device for performing immunoassays which comprises:

an immunosorbing member comprising a member of an immunological pair, defined as a mip, non-diffusively bound to at least a portion of a bibulous support; and a liquid absorbing member comprising a bibulous material in liquid receiving relationship with said immunosorbing member and extending transversely therefrom, wherein at least the portion of said liquid absorbing member about said immunosorbing member is enclosed in an impermeable enclosure to inhibit contact with solutions except through said immunosorbing member and said immunosorbing member has a relatively small liquid holding capacity as compared to said liquid absorbing member;

wherein said immunosorbing member and said liquid absorbing member are a single strip, said immunosorbing member being at the end of said single strip.

87. An assay device according to claim 86, wherein bound to said bibulous support is an enzyme.

88. An assay device according to claim 86, wherein bound to said mip is a labeled form of a homologous mip, substantially saturating all of the binding sites of said mip bound to said support.

89. An immunoassay kit comprising an assay device according to claim 86 in combination with a labeled mip separate from said assay device, wherein said labeled mip is the same as or complementary to said mip bound to said bibulous support, said labeled mip and said bound mip are present in amounts to substantially optimize the signal observed at said immunosorbing member.

90. A kit according to claim 89, wherein said label is an enzyme and including in combination, an enzyme substrate capable of providing a fluorescent or visible light absorptive product.

91. A kit according to claim 90, wherein said labeled mip is radioactively labeled mip.

* * * * *